US005227499A

United States Patent [19]
McGowan et al.

[11] Patent Number: 5,227,499
[45] Date of Patent: Jul. 13, 1993

[54] SUBSTITUTED SQUARYLIUM DYES, AND PROCESSES AND INTERMEDIATES FOR THE PREPARATION THEREOF

[75] Inventors: Donald A. McGowan, Bedford; Mark R. Mischke, Arlington; Stephen J. Telfer, Arlington, all of Mass.

[73] Assignee: Polaroid Corporation, Cambridge, Mass.

[21] Appl. No.: 795,341

[22] Filed: Nov. 20, 1991

[51] Int. Cl.$^5$ .................. C07D 311/58; C07D 309/34; C07D 335/06; C07D 345/00
[52] U.S. Cl. .................... 549/404; 549/415; 549/408; 549/398; 549/220; 549/218; 549/28; 549/23; 549/13; 549/5; 548/525; 548/517; 548/454; 546/207; 546/196; 546/66; 544/151; 544/149; 544/145; 540/1
[58] Field of Search .................. 549/404, 5, 13, 23, 549/28, 218, 220, 398, 408, 415; 548/525, 517, 454; 546/287, 196, 66; 544/151, 149, 145; 540/1

[56] References Cited

U.S. PATENT DOCUMENTS

| | | | |
|---|---|---|---|
| 4,343,948 | 8/1982 | Kawamura et al. | 549/13 |
| 4,508,811 | 4/1985 | Gravesteijn et al. | 430/270 |
| 4,602,263 | 7/1986 | Borrer et al. | 346/201 |
| 4,663,518 | 5/1987 | Borrer et al. | 235/487 |
| 4,720,449 | 1/1988 | Borrer et al. | 430/338 |
| 4,826,976 | 5/1989 | Borrer et al. | 544/58.4 |
| 4,960,901 | 10/1990 | Borrer et al. | 548/207 |

FOREIGN PATENT DOCUMENTS 58-220143 12/1983 Japan.
61-167681 7/1986 Japan.

OTHER PUBLICATIONS

Bellus, D., Syntheses of Highly Oxidized Cyclobutanes via [2+2] Cycloaddition Reactions of Ketenes, in West, R. (ed.), Oxocarbons, Academic Press (1980), pp. 169–184.

(List continued on next page.)

*Primary Examiner*—Nicky Chan
*Attorney, Agent, or Firm*—David J. Cole

[57] ABSTRACT

Squarylium compounds of the formula:

in which:
$Q^1$ and $Q^2$ are each a Chromophoric group having an unsaturated system conjugated with the squarylium ring and such that in the compounds of formulae $Q^1CH_2R^1$ and $Q^2CH_2R^2$ the methylene hydrogens are active hydrogens;
$R^1$ and $R^2$ are each independently a hydrogen atom or an aliphatic or cycloaliphatic group; and
$R^3$, $R^4$ and $R^5$ are each independently a hydrogen atom, or an aliphatic, cycloaliphatic, aromatic or heterocyclic group, or an electron-withdrawing group able to lower the electron density at the carbon atom to which it is attached, subject to the provisoes that:
two of $R^3$, $R^4$ and $R^5$ may form a divalent group of which a single atom is double bonded to the carbon atom to which the two groups are attached, or all three of $R^3$, $R^4$ and $R^5$ may form a trivalent group of which a single atom is triple bonded to the carbon atom to which the three groups are attached, or
two of $R^3$, $R^4$ and $R^5$ may, together with the carbon atom to which they are attached, form a ring, or all three of $R^3$, $R^4$ and $R^5$ may, together with the carbon atom to which they are attached, form an unsaturated ring,
are useful as near infra-red absorbers. The presence of the $-CR^3R^4R^5$ group on the squarylium ring enables changes in absorption wavelength to be achieved by modifications of this group, and also allows functional groups to be incorporated into the dye without changing the chromophoric groups.

15 Claims, 4 Drawing Sheets

OTHER PUBLICATIONS

Gerecht et al., Chem. Ber. 117(8), 2714–29 (1984).
Chickos et al., J. Am. Chem. Soc., 92, 5749 (1970).
Dehmlow et al., Chem. Ber. 113(1), 1–8 (1979).
Fatiadi, A. J., New Bond-Delocalized (Dicyanomethylidene)croconate Derivatives: "Croconate Violet" and Croconate Blue, in West, R. (ed.), Oxocarbons, Academic Press (1980).
Liebeskind et al., J. Org. Chem., 53, 2482 (1988).

SUBSTITUTED SQUARYLIUM DYES, AND PROCESSES AND INTERMEDIATES FOR THE PREPARATION THEREOF

BACKGROUND OF THE INVENTION

1. Field of the Invention

This invention relates to squarylium dyes, and processes and intermediates for the preparation thereof. More specifically, it relates to such dyes and intermediates in which two chromophoric groups occupy the 1- and 3-positions of the squarylium ring, while the 2-position bears a substituent in which a carbon atom is bonded directly to the squarylium ring.

2. References to Related Applications

Copending patent application U.S. Ser. No. 07/616,639, filed Nov. 21, 1990, and its continuation in part, application U.S. Ser. No. 07/795,038, of even date herewith, both assigned to the same assignee as the present application describe dyes comprising an inner salt of a compound of the formula:

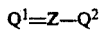

wherein:
$Q^1$ is a 4-(benz[b]-4H-pyrylium)methylidene, 4-(benz[b]-4H-thiopyrylium)methylidene or 4-(benz[b]-4H-selenopyrylium)methylidene grouping;
Z is a 1,3-(2-hydroxy-4-oxo-2-cyclobutylidene) or 1,3-(2-hydroxy-4,5-dioxo-2-cyclopentylidene) ring; and
$Q^2$ is a 4-(benz[b]-4H-pyran-4-ylidene)methyl, 4-(benz[b]-4H-thiopyran-4-ylidene)methyl or 4-(benz[b]-4H-selenopyran-4-ylidene)methyl grouping;
wherein at least one of the groupings $Q^1$ and $Q^2$ carries at its 2-position a substituent in which a non-aromatic carbon atom is bonded directly to the benzpyrylium, benzthiopyrylium or benzselenopyrylium nucleus, subject to the proviso that if this 2-substituent contains an aromatic nucleus, this aromatic nucleus is not conjugated with the benzpyrylium, benzthiopyrylium or benzselenopyrylium nucleus to which it is attached. These dyes have high absorptions in the near infra-red, and improved solubility in semi-polar solvents and plastics. The dyes disclosed in these applications include certain infra-red dyes used in the thermal imaging medium described below with reference to FIG. 4.

Copending application U.S. Ser. No. 07/696,222, filed May 6, 1991 and assigned to the same assignee as the present application, describes and claims the squarylium compounds of formulae D, E, J and K described below with reference to FIG. 1, together with similar compounds containing different heterocyclic nuclei, and squarylium compounds of the formula:

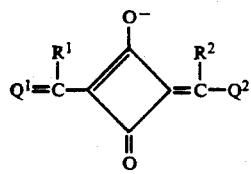

wherein $Q^1$ and $Q^2$ are each independently a heterocyclic nucleus such that in the compounds of formulae $Q^1CH_2R^1$ and $Q^2CH_2R^2$ the methylene hydrogens are active hydrogens, the atoms of $Q^1$ and $Q^2$ which are bonded directly to the $CR^1$ and $CR^2$ groupings respectively each being part of an aromatic ring, and $Q^1$ and $Q^2$ are different, and $R^1$ and $R^2$ are each independently a hydrogen atom or an aliphatic or cycloaliphatic group. The disclosure of this copending application is discussed below in more detail with reference to FIG. 1.

Copending applications U.S. Ser. Nos. 07/695,641; 07/696,196 and 07/695,932, all filed May 6, 1991 and all assigned to the same assignee as the present application, describe and claim imaging media comprising a color-forming layer comprising a thermal color-forming composition adapted to undergo a change of color upon increase in the temperature of the color-forming layer above a color-forming temperature for a color-forming time. Preferred imaging media described in these three applications comprise three separate color-forming layers containing yellow, cyan and magenta thermal color-forming compositions; each of these color-forming compositions comprises a color-forming compound which undergoes a change of color upon heating above the color-forming temperature for the color-forming time, and an infra-red absorber (which may be referred to hereinafter as an infra-red dye) capable of absorbing infra-red radiation and thereby generating heat in the color-forming layer. The three color-forming layers use infra-red absorbers absorbing at differing wavelengths so that each color-forming layer can be imaged independently; for example, specific imaging media disclosed in these three applications use infra-red absorbers having peak absorptions at approximately 792, 822 and 869 nm.

Copending application U.S. Ser. No. 07/795,034, of even date herewith and assigned to the same assignee as the present application, describes infra-red dyes generally similar to those of the present invention, but in which the 2-substituent on the squarylium ring is an amino or substituted amino group. The dyes described in this Application include the 2-aminosquarylium dye used in the thermal imaging medium described below with reference to FIG. 4.

Copending application U.S. Ser. No. 07/795,101, of even date herewith, by Rita S. Shon Baker et al. and assigned to the same assignee as the present application, describes and claims thermal imaging media generally similar to those described in the aforementioned applications U.S. Ser. Nos. 07/695,641; 07/696,196 and 07/695,932 but in which at least one imaging layer contains a metal cation. Preferred imaging media described in this application have imaging layers containing zinc acetate, as described below with reference to FIG. 4.

The disclosures of all the aforementioned copending applications are herein incorporated by reference.

DESCRIPTION OF THE PRIOR ART

It is known that compounds in which two chromophoric groups are linked by a pentamethine chain, the three central carbon atoms of which form part of a squarylium ring, are useful as dyes, especially near infra-red dyes. (The term "near infra-red" is used herein to mean electromagnetic radiation having a wavelength of about 700 to about 1200 nm.)

The term "chromophoric group" is used herein to mean a group containing a plurality of conjugated unsaturated linkages arranged so that the unsaturated linkages are conjugated with the squarylium ring via the unsaturated (sp$^2$) meso carbon atom lying between the chromophoric group and the squarylium ring, the chromophoric group being such that the squarylium dye has substantial absorption of visible or infra-red radiation.

For example, Japanese Patent Application No. 103,604/82 (Publication No. 220,143/83, published Dec. 21, 1983), discloses a broad class of bis-heterocyclic pentamethine dyes in which the central three carbon atoms of the pentamethine chain form part of a squarylium or croconylium ring. The heterocyclic nuclei can be pyrylium, thiopyrylium, selenopyrylium, benzpyrylium, benzthiopyrylium, benzselenopyrylium, naphthopyrylium, naphthothiopyrylium or naphthoselenopyrylium nuclei, which can be substituted with alkyl, alkoxy, aryl or styryl groups.

Japanese Patent Application No. 60-8730 (Publication No. 167,681/86, published Jul. 29, 1986), discloses bis(4-benz[b]thiopyrylium) pentamethine dyes in which the central three carbon atoms of the pentamethine chain form part of a squarylium ring. The dyes are intended for use as infra-red absorbers.

U.S. Pat. No. 4,508,811, issued Apr. 2, 1985, describes an optical recording element in which the recording layer comprises a bis(2,6-dialkyl)pyrylium or -thiopyrylium squarylium salt.

The squarylium dyes disclosed in these Japanese applications and U.S. patent are capable of achieving high extinction coefficients in the near infra-red range. However, such squarylium dyes suffer from a number of disadvantages. Many of these prior art dyes have low solubility in most plastics and/or in semi-polar solvents (for example, methyl ethyl ketone and methylene chloride) from which they need to be deposited to form imaging media. Thus, it is difficult to dissolve or disperse the absorber in a plastic without forming large aggregates and without adversely affecting other properties of the plastic.

A related disadvantage is that, unless specific functional groups are provided on the chromophoric groups (and the presence of such functional groups on the chromophoric groups may cause problems in the synthesis of the compounds from which the chromophoric groups are derived, or in the condensation of these compounds with squaric acid or its derivatives to form the final dyes), there is no convenient site (or "handle") on the squarylium dye for attachment of functional groups. Attachment of functional groups to the squarylium ring may be desirable, for example, to change the solubility of the dye in, or its compatibility with, various media, or to permit the dye to be chemically bonded to other materials.

Thirdly, among the squarylium dyes disclosed in these Japanese applications and U.S. patent, it may be difficult to find a dye which absorbs at the precise wavelength required for a particular application. For example, when choosing infra-red absorbers for use in imaging media such as those described in the aforementioned applications U.S. Ser. Nos. 07/695,641; 07/696,196 and 07/695,932, the need for independent addressing of the three color-forming layers, coupled with the widths of the peaks (typically the full-width-half-maximum (FWHM) of these peaks is about 35–40 nm) and the limited wavelength range over which present semiconductor lasers can be produced economically, mean that it is often necessary to find an infra-red absorber which has an absorption peak within a narrow range (say 10–15 nm) and which meets all the other requirements of stability, solubility and compatibility with other components of the imaging medium required for use in such an imaging medium. It is often difficult if not impossible to find a squarylium dye from among those disclosed in the Japanese applications and U.S. patent which absorbs within such a narrow wavelength range.

The aforementioned disadvantages of earlier prior art squarylium dyes are greatly reduced in the dyes described in the aforementioned applications U.S. Ser. Nos. 07/616,639, 07/795,038 and 07/696,222. The 2-non-aromatic substituted dyes described in applications U.S. Ser. Nos. 07/616,639 and 07/795,038, are substantially more soluble than the corresponding 2-phenyl dyes, while the asymmetric dyes which can be synthesized in good yields by the processes described in application U.S. Ser. No. 07/696,222 greatly ease the task of finding a dye which absorbs at a desired wavelength, since the ability to change the two chromophoric groups independently gives an additional degree of freedom, as compared with earlier dyes in which the two chromophoric groups were the same. However, neither of these copending applications describes dyes in which functional groups are provided on the squarylium ring itself. Furthermore, there are still situations in which it would be advantageous to provide dyes with even greater solubility in certain media than those described in applications U.S. Ser. Nos. 07/616,639 and 07/795,038, and it would also be advantageous to provide some way in which the dyes disclosed in applications U.S. Ser. Nos. 07/616,639, 07/795,038 and 07/696,222 could be "tuned" by shifting their infra-red absorption peaks over substantial ranges (say 100 nm) in order to assist in providing dyes having absorptions within desired ranges. Furthermore, when providing infra-red dyes for use in thermal imaging media such as those described in the aforementioned applications U.S. Ser. Nos. 07/695,641; 07/696,196 and 07/695,932, in which three infra-red dyes having widely-spaced absorptions are desired, it may be advantageous from a manufacturing point of view to use a set of infra-red dyes which are chemically closely related so that they share certain synthetic intermediates, with the necessary spacing in absorption wavelength among the final infra-red dyes being provided by varying substituents in the final dye.

It has now been found that providing a substituent in which a carbon atom is bonded directly to the squarylium ring in place of one of the oxygen atoms of the squarylium ring in squarylium dyes allows various functional groups to be incorporated conveniently into the dye, and may increase the solubility of the dye in, or its compatibility with, certain media. Also, substantial changes in the wavelength of maximum absorption of the dye can be achieved by varying the nature of the carbon-containing substituent. Accordingly, this invention is directed to these substituted squarylium dyes, and to processes and intermediates for the preparation of such dyes.

SUMMARY OF THE INVENTION

This invention provides a squarylium compound of the formula:

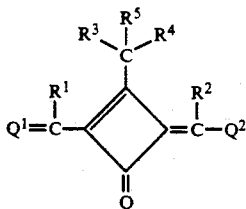

(I)

in which:

$Q^1$ and $Q^2$ are each a chromophoric group having an unsaturated system conjugated with the squarylium ring and such that in the compounds of formulae $Q^1CH_2R^1$ and $Q^2CH_2R^2$ the methylene hydrogens are active hydrogens;

$R^1$ and $R^2$ are each independently a hydrogen atom or an aliphatic or cycloaliphatic group; and $R^3$, $R^4$ and $R^5$ are each independently a hydrogen atom, or an aliphatic, cycloaliphatic, aromatic or heterocyclic group, or an electron-withdrawing group able to lower the electron density at the carbon atom to which it is attached, subject to the provisoes that:

two of $R^3$, $R^4$ and $R^5$ may form a divalent group of which a single atom is double bonded to the carbon atom to which the two groups are attached, or all three of $R^3$, $R^4$ and $R^5$ may form a trivalent group of which a single atom is triple bonded to the carbon atom to which the three groups are attached, or two of $R^3$, $R^4$ and $R^5$ may, together with the carbon atom to which they are attached, form a ring, or all three of $R^3$, $R^4$ and $R^5$ may, together with the carbon atom to which they are attached, form an unsaturated ring.

This invention also provides a squaric acid derivative of the formula:

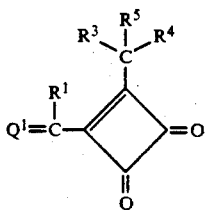

(II)

in which:

$Q^1$ is a chromophoric group having an unsaturated system conjugated with the squarylium ring and such that in the compound of formula $Q^1CH_2R^1$ the methylene hydrogens are active hydrogens;

$R^1$ is a hydrogen atom or an aliphatic or cycloaliphatic group; and $R^3$, $R^4$ and $R^5$ are each independently a hydrogen atom, or an aliphatic, cycloaliphatic, aromatic or heterocyclic group, or an electron-withdrawing group able to lower the electron density at the carbon atom to which it is attached, subject to the provisoes that:

two of $R^3$, $R^4$ and $R^5$ may form a divalent group of which a single atom is double bonded to the carbon atom to which the two groups are attached, or all three of $R^3$, $R^4$ and $R^5$ may form a trivalent group of which a single atom is triple bonded to the carbon atom to which the three groups are attached, or two of $R^3$, $R^4$ and $R^5$ may, together with the carbon atom to which they are attached, form a ring, or all three of $R^3$, $R^4$ and $R^5$ may, together with the carbon atom to which they are attached, form an unsaturated ring.

The squarylium compounds of Formula I in which at least one of $R^3$, $R^4$ and $R^5$ is an electron-withdrawing group able to lower the electron density at the carbon atom to which it is attached are preferably synthesized in a somewhat different manner from the other squarylium compounds of Formula I. Accordingly, when it is necessary to distinguish between these two groups of dyes, the former may hereinafter be referred to as the "EW-dyes" of the invention, and the latter as the "non-EW-dyes". Similarly, the squaric acid derivatives of Formula II may be referred to as "EW-derivatives" and "non-EW-derivatives" depending upon the nature of the groups $R^3$, $R^4$ and $R^5$.

This invention also provides a process for the preparation of a EW squaric acid derivative of Formula II, which process comprises reacting a corresponding squaric acid derivative of the formula:

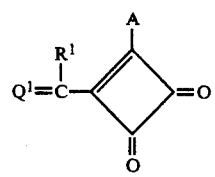

(III)

in which A is a chlorine or bromine atom, or an alkoxyl group, and $Q^1$ and $R^1$ are as defined above, with a compound of formula $CHR^3R^4R^5$, in which $R^3$, $R^4$ and $R^5$ are as defined above, in the presence of a base.

This invention also provides a process for the preparation of a squaric acid derivative of Formula II, which process comprises reacting a squaric acid derivative of the formula:

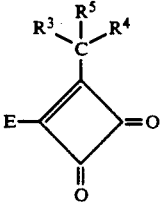

(IV)

in which $R^3$, $R^4$ and $R^5$ are as defined above, and E is an esterified hydroxyl group, with a compound of the formula $Q^1CH_2R^2$ in the presence of a base.

This invention also provides a process for the preparation of a squarylium compound of Formula I above, which process comprises reacting either a corresponding squaric acid derivative of either Formula II or Formula IV with at least one compound of formula $Q^2CH_2R^2$ in the presence of a base.

This invention also provides a process for generating heat in a medium comprising a dye of the present invention, which process comprises exposing at least part of the medium to infra-red actinic radiation of a frequency absorbed by the dye, whereby the radiation is absorbed by the dye and heat is generated within the parts of the medium exposed to the radiation.

Finally, this invention provides a thermal imaging medium comprising at least one imaging layer, the imaging layer comprising a color-forming compound which undergoes a change of color upon heating above a color-forming temperature for a color-forming time, the imaging layer further comprising a dye of the present invention.

It will be noted that the symbol $Q^1$ has been used for both a divalent grouping in Formulae I, II, III and IV and a monovalent grouping in the formula $Q^1CH_2R^1$. This apparent anomaly is due to the fact that the bond orders in the compounds of Formula I, II, III and IV are not integral. For example, when all the groups $R^1$-$R^5$ are electrically neutral, the dye A shown in FIG. 2 of the accompanying drawings is actually a resonance hybrid of the form shown and the similar form in which the positive charge resides on the oxygen atom of the other benzpyrylium nucleus (with contributions from other resonance forms). Thus, whether $Q^1$ is drawn as divalent or monovalent depends solely upon which of the contributing resonance forms is drawn, and similarly for $Q^2$. On the Other hand, the compounds of formula $Q^1CH_2R^1$, such as the salt B shown in FIG. 1, are not resonance hybrids to any significant extent, and thus in this formula $Q^1$ is correctly shown as monovalent. The $Q^1/Q^2$ nomenclature employed will thus be clear to skilled chemists.

When any one or more of $R^3$, $R^4$ and $R^5$ in the compounds of Formulae I and II is hydrogen, these hydrogen atoms are of course susceptible to being removed by relatively basic materials, and the compounds may thus be encountered in deprotonated forms depending upon the basicity of the medium containing the compound. Although the compounds of Formulae I and II are normally shown herein in their protonated forms, the invention extends to the deprotonated forms of these compounds. In particular, the compounds of Formula I in which $R^3$ is a hydrogen atom and both $R^4$ and $R^5$ are strongly electron-withdrawing groups (for example, cyano groups) are so readily deprotonated that, under substantially neutral conditions at room temperature, the dye is overwhelmingly in its deprotonated form. This deprotonated form is an inner salt in which the positive charge, which in compounds such as the dye A shown in FIG. 2 resides mostly upon the pyrylium oxygens, is balanced by the negative charge residing mostly upon carbon atom from which the proton $R^3$ has been removed; thus, unless other charged groups are present, such a dye is non-ionic. The discussion in the following four paragraphs assumes that the compounds of Formula I are present in their protonated form, but the consequences of deprotonation of the compound will readily be apparent to skilled chemists.

The compounds of Formula I produced by the processes of the present invention may be cationic, anionic or non-ionic. When none of the chromophoric groups $Q^1$ and $Q^2$ and the substituents $R^1$, $R^2$, $R^3$, $R^4$ and $R^5$ carries any charged substituents, the $Q^1Q^2$-substituted squarate moiety (hereinafter referred to simply as the "dye moiety") bears a single positive charge, and hence the dye is cationic. However, any one or more of the chromophoric groups $Q^1$ and $Q^2$ and the substituents $R^1$, $R^2$, $R^3$, $R^4$ and $R^5$ may carry a negatively or positively charged group (for example a —COO⁻ or trialkylammonium substituent), or, as already mentioned, if one of the groups $R^3$, $R^4$ and $R^5$ is a proton, this proton may be removed. If one or more negatively charged substituents is present, the dye will be non-ionic or anionic respectively.

When a counterion is present in a cationic or anionic dye of the present invention, the counterion may be any counterion which is not incompatible with the dye moiety and which thus provides a stable salt. The choice of counterion may be important in ensuring the solubility of the dye in various media, and reducing or preventing aggregation of the dye; minimizing aggregation of the dye is highly desirable since such aggregation can significantly reduce the apparent extinction coefficient of the dye in polymeric media.

Similarly, if the chromophoric group $Q^1$ or $Q^2$ does not carry any charged substituents (such nuclei being generally preferred in the present processes), the "compounds" $Q^1CH_2R^1$ and $Q^2CH_2R^2$ used in the present processes are actually cations. The counterion present may be any counterion which provides a stable salt and which does not interfere with the relevant reactions. Typically, large fluorinated anions, such as trifluoromethane sulfonate and tetrafluoroborate have been found to give good results in the present processes. The groups $Q^1$ and $Q^2$ may, however, bear charged substituents and thus in some cases $Q^1CH_2R^1$ and $Q^2CH_2R^2$ may be neutral compounds which do not require the presence of a counterion.

It may often be found convenient, for synthetic reasons, to prepare a desired moiety with one counterion and thereafter to effect a counterion exchange to form a different salt of the same moiety. Methods for such counterion ion exchange are well known to those skilled in the art.

DETAILED DESCRIPTION OF THE INVENTION

Figure 1:
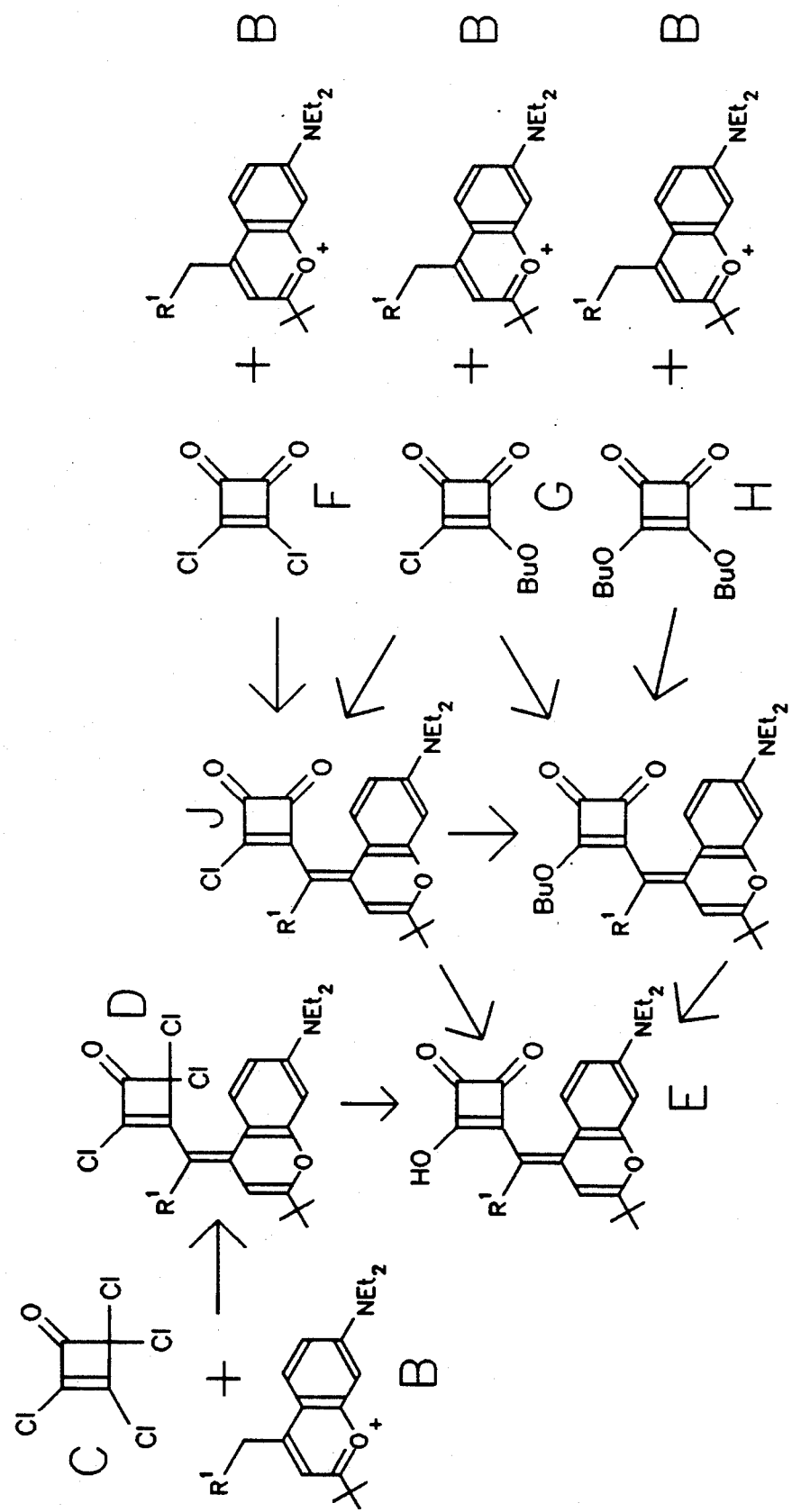
FIG. 1 of the accompanying drawings shows a synthetic scheme for the preparation of a starting material of Formula III used in the present invention by reactions described in the aforementioned application Ser. No. 07/696,222.
Figure 2:
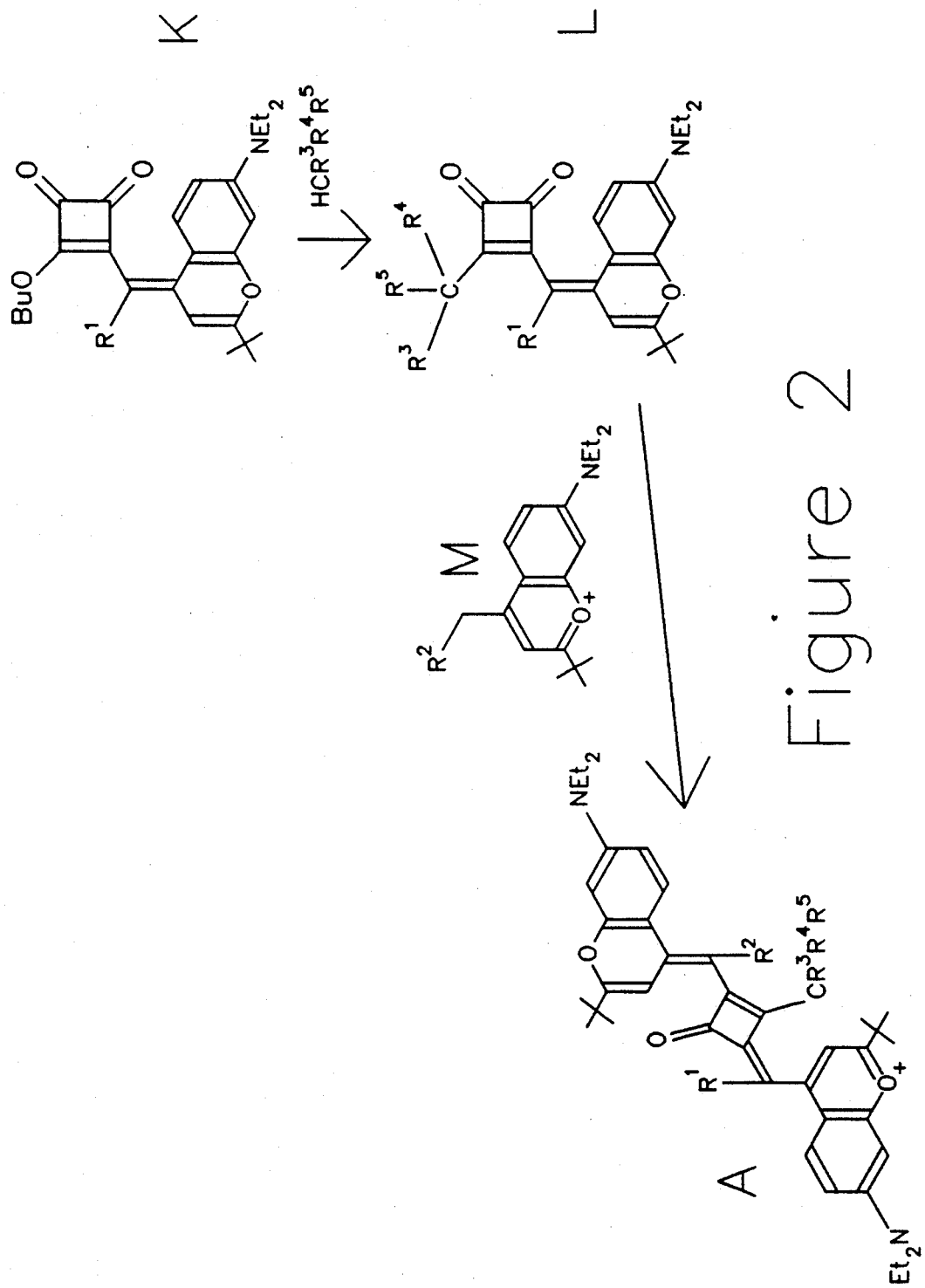
FIG. 2 shows the conversion of a starting material of Formula III to a squaric acid derivative of Formula II and thence to a squarylium compound of Formula I by reactions of the present invention.

The interrelationships among the various reactions of the present invention may best be seen from the accompanying drawings. FIGS. 1 and 2 show a synthetic scheme for the preparation of a squarylium compound (hereinafter referred to as "dye A") of Formula I, in which $Q^1$ is (in the resonance hybrid drawn) a 7-diethylamino-2-(1,1-dimethylethyl)-(benz[b]-4H-pyran-4-ylidene) grouping and $Q^2$ is a 4-[7-diethylamino-2-(1,1-dimethylethyl)-benz[b]pyrylium] grouping. The reactions shown in FIG. 1 are described in the aforementioned application Ser. No. 07/696,222, while the reactions shown in FIG. 2 are reactions of the present invention. Accordingly, the reactions shown in FIG. 1 will only be briefly described herein, and for fuller details the reader is referred to the copending application Ser. No. 07/696,222.

One form of the synthesis begins with the condensation of a 2,6-bis(1,1-dimethylethyl)-4-($R^1$-methyl)-7-diethylaminobenzpyrylium salt B (a compound of Formula $Q^1CH_2R^1$) with 2,3,4,4-tetrachlorocyclobut-1-en-2-one C to give the trihalosquaric acid derivative D. The tetrachloro compound C and its synthesis are described in Maahs et al., "Syntheses and Derivatives of Squaric Acid", Angew. Chem. Int. Ed., 5, 888–893 (1966). This reaction is conducted in the presence of a base, preferably triethylamine. As noted above, the anion of the salt B can be any anion which provides a stable salt and which does not interfere with the desired reaction; conveniently the tetrafluoroborate salt is used.

As may be seen from FIGS. 1 and 2, use of the 4-methylbenzpyrylium salt B ($R^1$ is a hydrogen atom) will produce a dye in which $R^1$ is hydrogen. If the 4-methyl group of the salt B is replaced with a different group of the formula —$CH_2R^1$, the corresponding dyes can be produced in which $R^1$ is an aliphatic or cycloaliphatic group; thus, for example, the use of a 4-ethyl salt gives a final dye in which $R^1$ is methyl. Similar variations in the group $R^2$ are produced by varying the 4-substituent in the benzpyrylium salt of Formula M (described below). The tetrabromo homologue may be used in place of the tetrachloro compound C.

In the next step of the synthesis, the trihalosquaric acid derivative D is hydrolyzed to the corresponding non-halogenated derivative E. Desirably, this hydrolysis is effected by heating the derivative D with triflic acid, then adding water.

Alternatively, the non-halogenated derivative E may be prepared by condensing the salt B with the diacid chloride (F), an ester/acid chloride (G) or a diester (H) of squaric acid (the butyl ester/acid chloride and diester are shown in FIG. 1), followed by hydrolysis of the resultant product. With both the monoacid chloride/monoester G and the diester H, this reaction requires the presence of a base to produce useful yields; with the more reactive diacid chloride F, this reaction can be conducted without base. The reaction of the diacid chloride F may also be catalyzed by a Lewis acid.

When the diacid chloride F is used as starting material in this reaction, the intermediate is J, the acid chloride of E, whereas when the diester H is used as starting material, the intermediate is K, the ester of E. When the ester/acid chloride G is used, both J and K are produced, but the production of this mixture poses no problems, since both compounds are readily hydrolyzed to give the derivative E. If desired, the acid chloride J may be treated with methanol to convert it to the ester K. Acid bromides may be used in place of the acid chlorides, and the group $R^1$ may be varied by changing the 4-substituent on the salt B, as described above.

In FIG. 2 there is shown the preferred reaction sequence used to prepare an EW-dye of the present invention. In this reaction sequence, the $CR^3R^4R^5$ group is introduced into the ester K using a carbanion —$CR^3R^4R^5$ (i.e., using the compound $HCR^3R^4R^5$ in the presence of a base to produce the corresponding substituted squaric acid derivative L. The reaction may also be conducted using the acid chloride J shown in FIG. 1 instead of the ester K.

The final step of the synthesis of the squarylium dye A is the condensation of the squaric acid derivative L with one mole of the appropriate compound of formula $Q^2CH_2R^2$; the compound in which $Q^2$ is a 2-(1,1-dimethylethyl)-7-diethylaminobenzpyrylium group is shown in FIG. 2. The conditions required for this reaction are substantially the same as those used for the prior art reactions in which two moles of a benzpyrylium salt are condensed with squaric acid to form a symmetric bis-benzpyrylium dye. Thus, this reaction is assisted by base, conveniently a tertiary amine, for example quinoline. The reaction is desirably conducted in solution in an alcohol, conveniently n-butanol.

Although the reaction L→A illustrated in FIG. 2 produces a dye A in which $Q^1$ is the same as $Q^2$, it will readily be apparent that this need not be the case, since the group $Q^1$ derived from compound B (FIG. 1) could be different from the group $Q^2$ derived from compound M. Thus, the synthesis shown in FIGS. 1 and 2 can be used to produce both symmetric dyes, in which $Q^1$ and $Q^2$ are the same, and asymmetric dyes in which these two groups are different.

In many cases, the synthesis of the final squarylium dye is most simply achieved by introducing the final $CR^3R^4R^5$ group during the preparation of the compound L; for example, when $R^3$ is a hydrogen atom and each of $R^4$ and $R^5$ is a cyano group, so that the compound $HCR^3R^4R^5$ is malononitrile, the reaction K→L proceeds well so that there is no difficulty in incorporating the final $CR^3R^4R^5$ group in this step of the synthesis. However, in other cases, the substituents $R^3$ and $R^4$ may be such that the compound $HCR^3R^4R^5$ will not react readily with the squaric acid derivative K. In such circumstances it may be preferred to use a different, more reactive compound $HCR^3R^4R^5$ in the reaction K→L, and then to modify $R^3$ and/or $R^4$ and/or $R^5$ either in the compound L or, desirably, in the final dye A.

Furthermore, the groups $R^3$, $R^4$ and $R^5$ may contain various functional groups, and some of these functional groups may be capable of interfering with one or both of the reactions K→L and L→A. For example, the reaction L→A depends upon the presence of active hydrogens in the compound $Q^2CH_2R^2$, and any functional groups within the groups $R^3$, $R^4$ and $R^5$ which contain active hydrogens may interfere with this reaction. In such cases, it may be necessary to modify the synthesis shown in FIG. 2 either by modifying the group $R^3$ and/or $R^4$ and/or $R^5$ in the dye A, or by blocking the functional groups in the compound $HCR^3R^4R^5$ and then unblocking these groups in the dye A.

Figure 3:
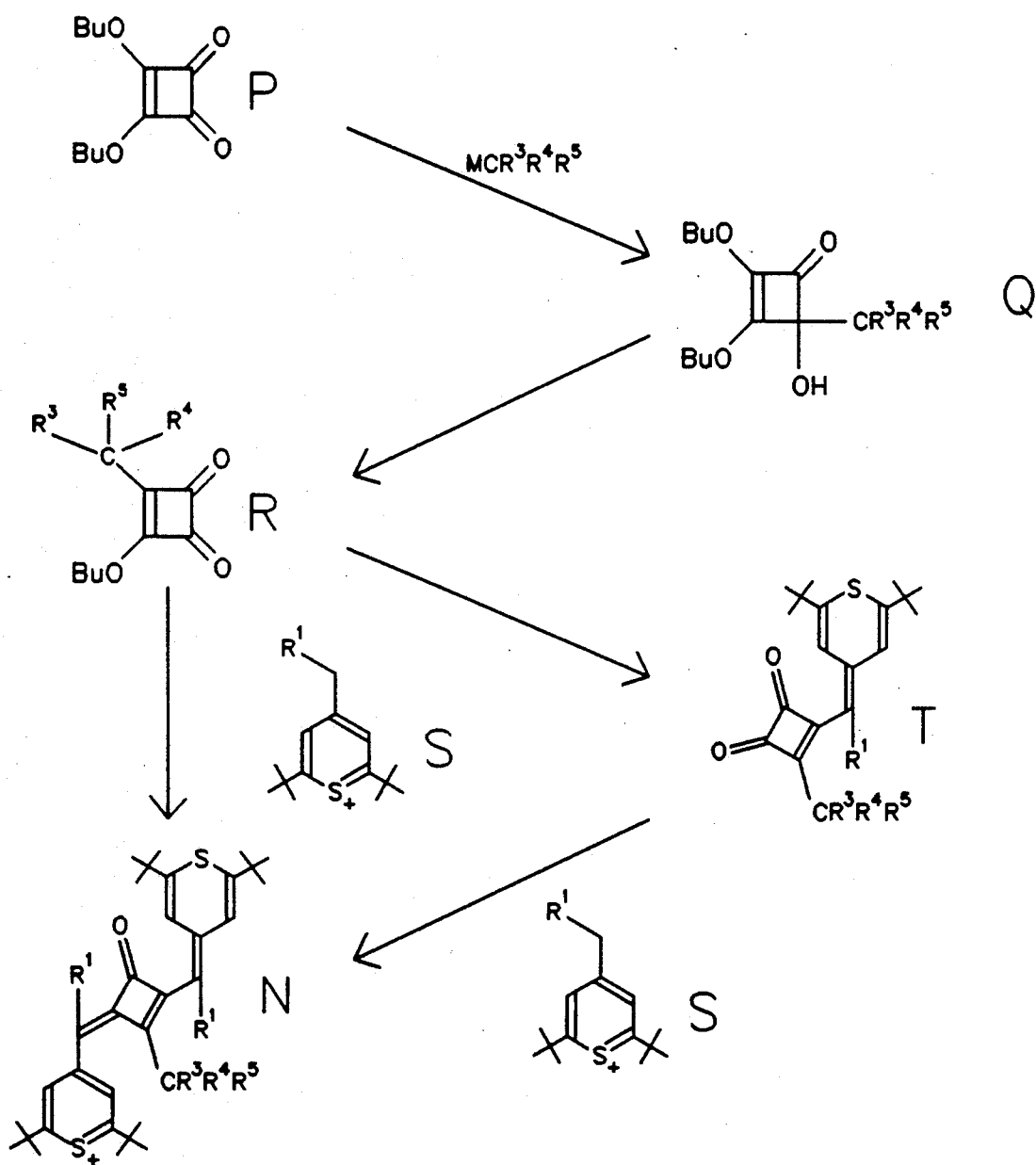
FIG. 3 shows the synthesis of a squarylium compound of Formula I from a corresponding squaric acid diester.

FIG. 3 shows an alternative synthesis of a dye N starting from a diester P of squaric acid (the dibutyl ester is illustrated in FIG. 3). The diester P is first condensed with a compound containing a negatively charged species $CR^3R^4R^5$; this compound is normally an organometallic compound, and preferably an organolithium compound. The reaction adds the —$CR^3R^4R^5$ group to one of the oxo groups of the diester P to produce the squaric acid derivative Q; to avoid disubstitution into both oxo groups, not more than the stoichiometric amount of the organometallic reagent should be used.

After being separated from unreacted starting material P and other by-products, the squaric acid derivative Q is treated with an acid, for example hydrochloric acid to convert it to the squaric acid derivative R. Although it is possible to simply add acid to the reaction mixture resulting from the treatment of the diester P with the organometallic reagent, this course is not recommended, since the squaric acid derivative R produced may be contaminated with unreacted ester P, and P and R are so similar that it is extremely difficult to separate them, even by chromatography.

In one version of the synthesis shown in FIG. 3, the squaric acid derivative R is then condensed with two moles of a compound S of formula $Q^1CH_2R^1$ (the salt in which $Q^1$ is a 2,6-bis(1,1-dimethylethyl)thiopyrylium group is illustrated in FIG. 3) to produce the final symmetrical dye N. The reaction R→N may be carried out under the same conditions as the reaction L→A described above with reference to FIG. 2. Also, the synthesis shown in FIG. 3 may be modified to include changes in the group $R^3$ and/or $R^4$ in the dye N, and the blocking of functional groups, as discussed above with reference to FIG. 2.

Alternatively, the squaric acid derivative R may be condensed with only one mole of a salt S of formula $Q^1CH_2R^1$ to produce a monocondensed intermediate T; the conditions required for this reaction are substantially the same as those for the reaction B+H→K described above with reference to FIG. 1. This intermediate T may then be condensed with a second mole of the appropriate salt S to produce the final dye N, using the same conditions as for the reaction R→N. Obviously, although FIG. 3 shows the same salt being condensed with both R and T, two different salts could be used in the two reactions, thereby permitting synthesis of asymmetric dyes in which $Q^1$ and $Q^2$ are different.

The syntheses shown in FIG. 3 may provide a more unambiguous synthesis of non-EW dyes of the invention than that shown in FIG. 2.

The nomenclature used herein for the dyes of the invention is that used by Chemical Abstracts and is thus apparently that recommended by IUPAC. However, in view of the difficulty of naming some of the present dyes in which the group $CR^3R^4R^5$ is capable of being deprotonated, it is believed that some explanation of this nomenclature may be helpful. A typical EW-dye of this present invention will be written herein as:

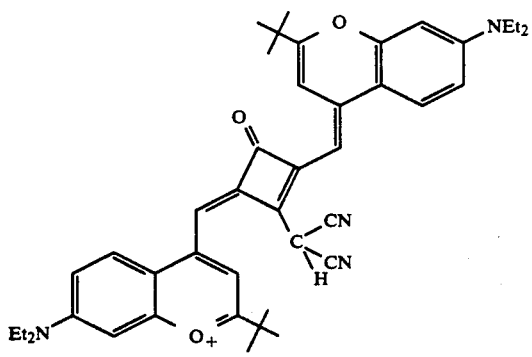

Under substantial neutral conditions, such as in the polymeric binders used in most thermal imaging media, this dye is believed to exists substantially in a zwitterionic form, to which the main contributing form is of course:

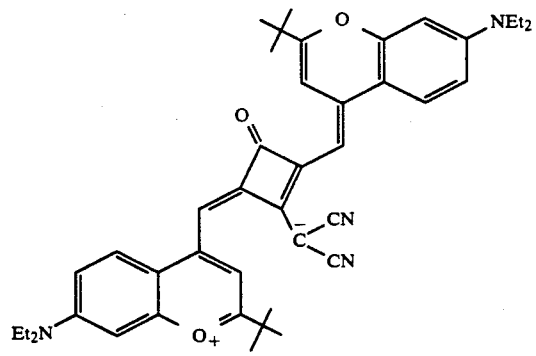

and the corresponding form with the positive charge on the other pyrylium nucleus. This dye is, however, named as the inner salt of the hypothetical hydroxide:

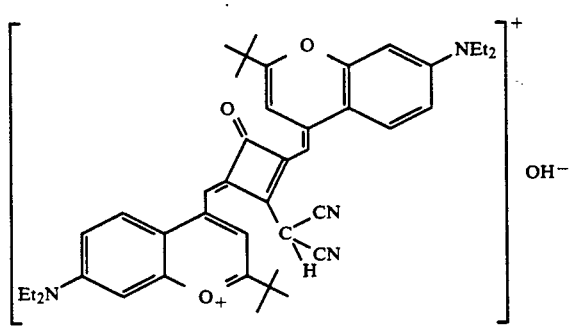

and is thus named 4-[[4-dicyanomethyl-3-[[7-d iethylamino-2-[1,1-dimethylethyl]benz[b]-4H-pyran-4-ylidene]methyl]-cyclobut-3-en-2-one-1-ylidene]methyl]-7-diethylamino-2-[1,1-dimethylethyl]-benz[b-]pyrylium hydroxide inner salt dye. Salts of compounds of the invention with other bases are named in a corresponding manner.

As already indicated, a wide range of groups $R^3$, $R^4$ and $R^5$ can be present in the squarylium dyes of the present invention. Thus, for example, $R^3$, $R^4$ and $R^5$ can each independently be a hydrogen atom or an alkyl or acyl group, or one of these groups can be a hydrogen atom and the others can each be a strongly electron-withdrawing group, such as a cyano group. Any one or more of $R^3$, $R^4$ and $R^5$ can also each be an alicyclic group (for example, a cyclohexyl group), an aromatic group (for example, a phenyl group), or a heterocyclic group (for example, a piperidinyl group), or alternatively two of $R^3$, $R^4$ and $R^5$, together with the intervening carbon atom, may form an alicyclic or heterocyclic group, for example a cyclohexyl or morpholinyl group, or two of $R^3$, $R^4$ and $R^5$, may form a single group which is double-bonded to the carbon attached to the squarylium nucleus. Also, all three of $R^3$, $R^4$ and $R^5$, together with the intervening carbon atom, may form an unsaturated ring system, for example a phenyl group, or all three of $R^3$, $R^4$ and $R^5$, may form a single group which is triple-bonded to the carbon attached to the squarylium nucleus; thus, for example, the —$CR^3R^4R^5$ grouping could be an acetylenic group.

Any of these groups $R^3$, $R^4$ and $R^5$ may be unsubstituted or substituted; it is one of the advantages of the dyes of the present invention that the carbon attached to the squarylium ring, and the groups $R^3$, $R^4$ and $R^5$ attached thereto, provide convenient sites to which a variety of groups may be attached in order to modify the properties of the dye, without having to change the chromophoric groups $Q^1$ and $Q^2$. Thus, the groups $R^3$, $R^4$ and $R^5$ may contain substituents which affect the solubility of the dye in various media. For example, if it desired to increase the solubility of the dye in highly polar solvents, the groups $R^3$, $R^4$ and $R^5$ may contain sulfonic acid or quaternary ammonium groups. On the other hand, if it desired to increase the solubility of the dye in non-polar solvents, the groups $R^3$, $R^4$ and $R^5$ may be unsubstituted long-chain alkyl groups.

The groups $R^3$, $R^4$ and $R^5$ may also contain groups which permit linking the dye to other materials, thereby permitting, for example, the dye to be incorporated into a polymer.

The substitution of the $-CR^3R^4R^5$ group for the $-O^-$ group present in the corresponding unsubstituted squarylium dye affects the spectrum of the squarylium dye. Among the dyes of the present invention, the greater the $\pi$-electron donation from the 2-substituent into the conjugated chromophore, the longer the wavelength ($\lambda_{max}$) of maximum absorption of the dye. For example, the dye A shown in FIG. 2 in which $R^1$ and $R^2$ are hydrogen atoms and the $-CR^3R^4R^5$ group is an ethyl group has a substantially shorter $\lambda_{max}$ (752 nm) than the corresponding dye in which $R^3$ and $R^4$ are each a cyano group and $R^5$ is a hydrogen atom (850 nm). The α-carbon atom of the ethyl group has no $\pi$-orbital available for interaction with the chromophore, whereas the dicyanomethyl group, which is deprotonated under neutral conditions, has such $\pi$-orbitals available for donation to the chromophore. Thus, in this series of dyes, modification of the 2-substituent permits variation ("tuning") of $\lambda_{max}$ over a range of about 100 nm.

Because of this dependency of $\lambda_{max}$ upon the 2-substituent, in dyes of the invention in which the $-CR^3R^4R^5$ group is capable of being deprotonated, there may be a substantial difference in $\lambda_{max}$ between the protonated and deprotonated forms of the dye. Accordingly, when absorption at a specific wavelength is desired, care should be taken to ensure that the dye is in the desired protonated or deprotonated form, for example by placing the dye in an acidic or basic medium.

Although the invention has been shown in the accompanying drawings and described above with reference to compounds in which $Q^1$ and $Q^2$ are each a pyrylium or benzpyrylium nucleus, it will be apparent that both $Q^1$ and $Q^2$ can each independently be any chromophoric group such that in the compounds of formulae $Q^1CH_2R^1$ and $Q^2CH_2R^2$ the methylene hydrogens are active hydrogens, so that these methylene hydrogen atoms can undergo the condensations with squaric acid derivatives already described. It is preferred that the atoms of $Q^1$ and $Q^2$ which are bonded directly to the $CR^1$ and $CR^2$ groupings respectively each be part of an aromatic ring. For example, $Q^1$ and $Q^2$ may each independently be an imidazole, benzimidazole, thiazole, benzthiazole, oxazole, benzoxazole, 2- or 4-pyridinium, 2- or 4-quinolinium or indolinium nucleus. Desirably, at least one, and preferably both, of $Q^1$ and $Q^2$ is a non-nitrogenous heterocyclic nucleus, especially preferred nuclei being pyrylium, thiopyrylium, selenopyrylium, benzpyrylium, benzthiopyrylium and benzselenopyrylium nuclei. Such nuclei be either the 2- or 4-isomers, although the latter are preferred.

In a particularly preferred group of dyes of Formula I, $Q^1$ and/or $Q^2$ is a 2,6-dialkylpyrylium, -thiopyrylium or -selenopyrylium nucleus, in which each of the alkyl groups contains not more than about 8 carbon atoms, especially those in which $Q^1$ and/or $Q^2$ is a 2,6-di-tertiary butylpyrylium, -thiopyrylium or -selenopyrylium nucleus. The presence of these nuclei in the dyes has been found to provide good solubility in polymeric media and high extinction coefficients.

Another preferred group of dyes of Formula I are those in which $Q^1$ and/or $Q^2$ is a 4-benzpyrylium nucleus, desirably such a nucleus which carries at its 2-position a substituent in which a non-aromatic carbon atom is bonded directly to the benzpyrylium nucleus, subject to the proviso that if this 2-substituent contains an aromatic nucleus, this aromatic nucleus is not conjugated with the benzpyrylium nucleus. Preferred 2-substituents are substituted or unsubstituted alkyl or cycloalkyl groups, desirably ones in which the carbon atom which is directly attached to the benzpyrylium nucleus carries not more than one hydrogen atom. Examples of suitable 2-substituents include isopropyl, sec-butyl, tert-butyl, 2-ethyl-2-methylbutyl, 2,2-dimethylbutyl, cyclohexyl, 6,6-dimethylbicyclo-[3.1.1]hept-2-en-2-yl, bicyclo[2.2.1]hept-2-en-5-yl and adamantyl groups.

Desirably, the benzpyrylium nucleus also carries at its 7-position a substituent in which an element of Group 5A, 6A or 7A of the Periodic Table is directly connected to the benzpyrylium nucleus, subject to the proviso that when this element of Group 5A, 6A or 7A is at least divalent, the 7-substituent may comprise at least one saturated heterocyclic ring containing said element of Group 5A, 6A or 7A, this saturated heterocyclic ring optionally being fused to the phenyl ring of the associated benzpyrylium nucleus; especially preferred 7-substituents are alkoxy groups containing not more than about 12 carbon atoms, or disubstituted amino or disubstituted phosphino groups, wherein each of the substituents on the or each disubstituted group comprises an alkyl group containing not more than about 6 carbon atoms, or the two substituents on any one disubstituted group together form, with the nitrogen or phosphorus atom thereof, a heterocyclic ring system, this ring system optionally being fused to the benzpyrylium nucleus which carries the disubstituted amino or phosphino substituent. Examples of suitable 7-substituents include dialkylamino wherein each of the alkyl groups contains not more than about 4 carbon atoms, piperidino, indolinyl, morpholino and $-N[-(CH_2)_3-]_2$ groups, subject to the proviso that when one or both of the amino groups is a $-N[-(CH_2)_3-]_2$ group, the ends of the trimethylene groups remote from the nitrogen atom are joined to the 6- and 8-positions of the benzpyrylium nucleus carrying the nitrogen atom, so that the $-N[-(CH_2)_3-]_2$ group and the benzene ring of the benzpyrylium nucleus together form a julolidine ring system. As described in the aforementioned applications U.S Ser. Nos. 07/616,639 and 07/795,038, dyes containing such 4-benzpyrylium nuclei have desirable properties, including solubility in polymeric media and high extinction coefficients.

Although $R^1$ and $R^2$ may be other groups, for example cycloalkyl groups, it is preferred that these two groups each independently be a hydrogen atom or an alkyl group containing not more than about 6 carbon atoms.

Specific preferred dyes of Formula I are those in which:

a. $Q^1$ is a 7-diethylamino-2-[1,1-dimethylethyl]-benz[b]-4H-pyran-4-ylidene grouping, $Q^2$ is a 7-diethylamino-2-[1,1-dimethylethyl]benz[b]-4H-pyrylium grouping, $R^1$ and $R^2$ are each a hydrogen atom, $R^3$ and $R^4$ are each a cyano group, and $R^5$ is a hydrogen atom, namely 4-[[4-dicyanomethyl-3-[[7-diethylamino-2-[1,1--dimethylethyl]benz[b]-4H-pyran-4-ylidene]-methyl]-cyclobut-3-en-2-one-1-ylidene]methyl]--7-diethylamino-2-[1,1-dimethylethyl]benz[b]pyrylium hydroxide inner salt;

b. $Q^1$ is a 2,6-bis-[1,1-dimethylethyl]-4H-thiopyran-4-ylidene grouping, $Q^2$ is a 4-[2,6-bis-[1,1-dimethylethyl]-4H-thiopyrylium grouping, $R^1$ and $R^2$ are each a hydrogen atom, $R^3$ and $R^4$ are each a cyano group, and $R^5$ is a hydrogen atom, namely 4-[[4-dicyanomethyl-3-[[2,6-bis-[1,1-dimethylethyl]-thio-4H-pyran-4-ylidene]methyl]-cyclobut-3-en-2-one-1-ylidene]methyl]-2,6-bis-[1,1-dimethylethyl]-thiopyrylium hydroxide inner salt;

c. $Q^1$ is a 7-diethylamino-2-[1,1-dimethylethyl]-benz[b]-4H-pyran-4-ylidene grouping, $Q^2$ is a 7-diethylamino-2-[1,1-dimethylethyl]-benz[b]-4H-pyrylium grouping, $R^1$ and $R^2$ are each a hydrogen atom and the $CR^3R^4R^5$ grouping is a phenyl group, namely a 4-[[3--[[7-diethylamino-2-[1,1-dimethylethyl]benz[b]-4H-pyran-4-ylidene]methyl]-2-phenyl-2-cyclobuten-1-ylidene]methyl]-7-diethylamino-2-[1,1-dimethylethyl]-benz[b]pyrylium salt; and d. $Q^1$ is a 7-diethylamino-2-[1,1-dimethylethyl]-benz[b]-4H-pyran-4-ylidene grouping, $Q^2$ is a 7-diethylamino-2-[1,1-dimethylethyl]benz[b]-4H-pyrylium grouping, $R^1$ and $R^2$ are each a hydrogen atom, and the $CR^3R^4R^5$ grouping is an ethyl group, namely a 4-[[-3-[[7-diethylamino-2-[1,1-dimethylethyl]benz[b]-4H-pyran-4-ylidene]methyl]-2-ethyl-2-oyolobuten-1-ylidene]methyl]-7-diethylamino-2-[1,1-dimethylethyl]-benz[b]pyrylium salt.

Correspondingly, specific preferred squaric acid derivatives of Formula II are those in which:

a. $Q^1$ is a 7-diethylamino-2-[1,1-dimethylethyl]-benz[b]-4H-pyran-4-ylidene grouping, $R^1$ is a hydrogen atom, $R^3$ and $R^4$ are cyano groups, and $R^5$ is a hydrogen atom, namely 4-dicyanomethyl-3-[[7-diethylamino-2-[1,1-dimethylethyl]benz[b]-4H-pyran-4-ylidene]methyl]-cyclobut-3-en-1,2-dione, and salts thereof;

b. $Q^1$ is a 2,6-bis-[1,1-dimethylethyl]-4H-thiopyran-4-ylidene grouping, $R^1$ is a hydrogen atom, $R^3$ and $R^4$ are cyano groups, and $R^5$ is a hydrogen atom, namely 4-dicyanomethyl-3-[[2,6-bis-[1,1-dimethylethyl]-thio-4H-pyran-4-ylidene]methyl]-cyclobut-3-en-1,2-dione, and salts thereof;

c. $Q^1$ is a 7-diethylamino-2-[1,1-dimethylethyl]-benz[b]4H-pyran-4-ylidene grouping, $R^1$ is a hydrogen atom and the $CR^3R^4R^5$ grouping is a phenyl group, namely 3-[[7-diethylamino-2-[1,1-dimethylethyl]benz[b]-4H-pyran-4-ylidene]-methyl]-4-phenylcyclobut-3-en-1,2-dione; and d. $Q^1$ is a 7-diethylamino-2-[1,1-dimethylethyl]-benz[b]-4H-pyran-4-ylidene grouping, $R^1$ is a hydrogen atom and the $CR^3R^4R^5$ grouping is an ethyl group, namely 3-[[7-diethylamino-2-[1,1-dimethylethyl]-benz[b]-4H-pyran-4-ylidene]methyl]-4-ethylcyclobut-3-en-1,2-dione.

The dyes produced by the processes of the present invention may be used in any of the applications in which prior art near infra-red absorbers have been used. Thus, the dyes may be used as dyes in printing inks intended to provide markings which can be read under near infra-red radiation, for example, on packages of consumer items intended to be scanned by near infrared laser scanners. At least some of the present dyes may also be useful as charge transfer materials for use in xerography, electrophotography and similar processes, and as laser dyes.

However, because of their high extinction coefficients in the near infra-red region, the dyes produced by the present processes are especially useful in processes for generating heat in a medium; in such a process at least part of the medium is exposed to near infra-red actinic radiation of a frequency absorbed by the dye, so that the radiation is absorbed by the dye and heat is generated within the parts of the medium exposed to the radiation. Typically, in such a process, the radiation is provided by a laser. The medium may also comprise a thermally sensitive material capable of undergoing a color change upon exposure to heat; the medium is exposed imagewise to the radiation, and the heat generated by the dye is sufficient to effect a color change in the thermally sensitive material, so that an image is formed in the medium. Thus, for example, the present dyes may be used as the near infra-red absorbers in the thermal imaging processes described in U.S. Pat. Nos. 4,602,263 and 4,826,976, and in the aforementioned copending applications U.S. Ser. Nos. 07/695,641; 07/696,196 and 07/695,932. These imaging processes rely upon the irreversible unimolecular fragmentation of one or more thermally unstable carbamate moieties of an organic compound to effect a visually discernible color shift from colorless to colored, from colored to colorless or from one color to another.

In such a process, preferably the thermally sensitive material is originally substantially colorless and is converted by the heat generated to a colored material in exposed areas of the image. Multi-colored images may be produced using a heat-sensitive element containing an imaging layer of colorless imaging compound (leuco dye) for forming a yellow image, an imaging layer of colorless imaging compound for forming a cyan image, and an imaging layer of colorless imaging compound for forming a magenta image. Preferred leuco dyes, and processes for their preparation, are described in U.S. Pat. No. 4,663,518, and other preferred yellow-forming leuco dyes are described in application U.S. Ser. No. 07/548,223, filed Jun. 29, 1990.

In the production of such multi-color images, each imaging layer contains, in addition to the leuco dye, an infra-red absorber selected such that the three infra-red absorbers absorb radiation at different predetermined wavelengths above 700 nm sufficiently separated so that each imaging layer may be exposed separately and independently of the others by using infra-red radiation at the particular wavelengths selectively absorbed by the respective infra-red absorbers. As an illustration, the yellow, magenta and cyan precursors may have infrared absorbers associated therewith that absorb radiation at (say) 760 nm, 820 nm and 880 nm, respectively, and may be addressed by laser sources, for example, infrared laser diodes emitting radiation at these respective wavelengths so that the three imaging layers can be exposed independently of one another. While each layer may be exposed in a separate scan, it is usually preferred to expose all of the imaging layers simultaneously in a single scan using multiple laser sources of the appropriate wavelengths. Instead of using superimposed imaging layers, the heat-sensitive compounds and associated infra-red absorbers may be arranged in an array of side-by-side dots or stripes in a single recording layer.

A preferred imaging medium of this type will now be described, though by way of illustration only, with reference to FIG. 4 of the accompanying drawings, which is a schematic cross-section through the imaging medium. The thicknesses of the various layers shown in the drawing are not to scale.

Figure 4:
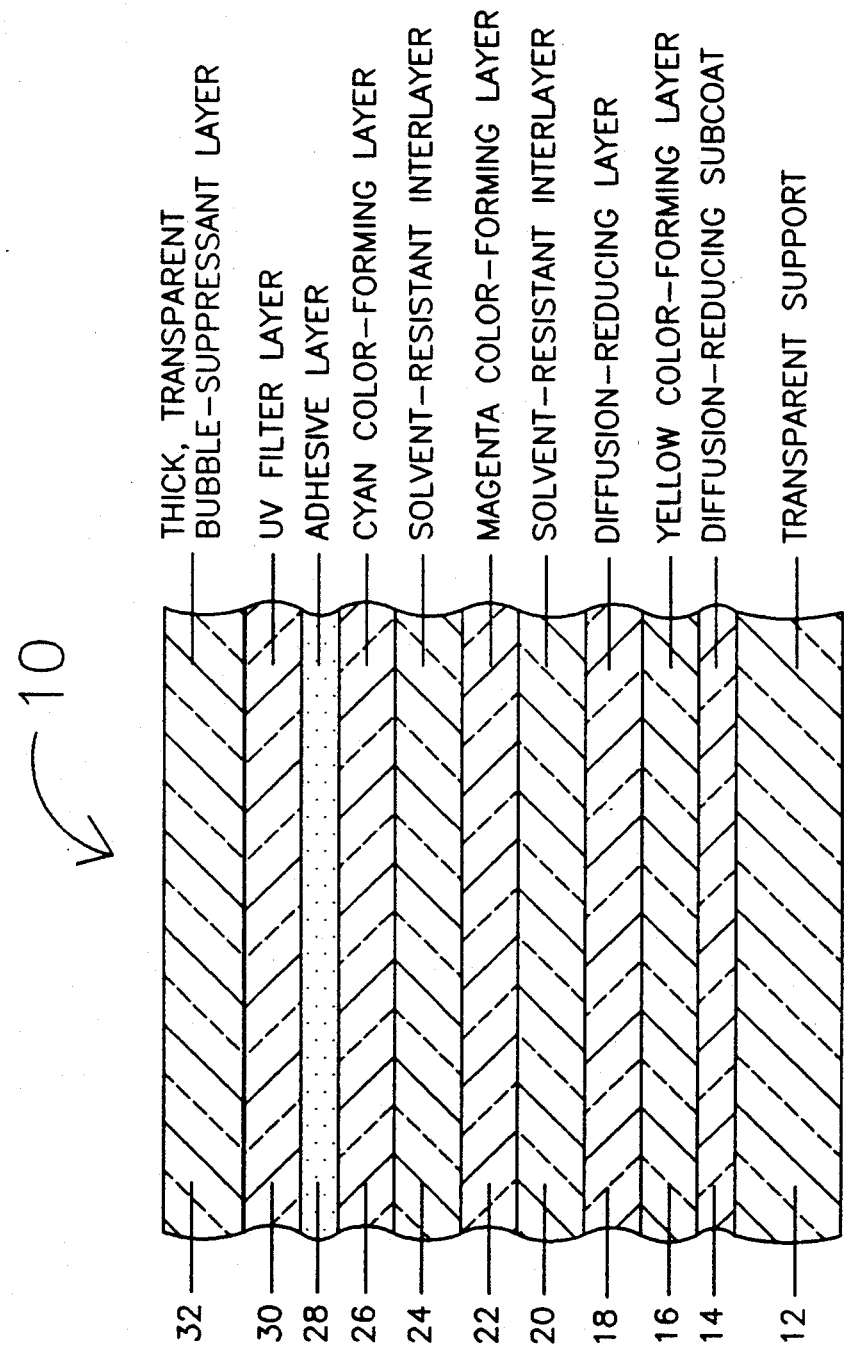
FIG. 4 shows a schematic cross-section through a preferred imaging medium of the present invention incorporating an infra-red dye of the present invention.

The imaging medium (generally designated 10) shown in FIG. 4 is intended for use in the production of transparencies and comprises a substantially transparent support 12 formed of 4 mil (101 μm) poly(ethylene terephthalate) (PET) film incorporating an ultra-violet absorber. Appropriate PET films are readily available commercially, for example as P4ClA film from DuPont de Nemours., Wilmington, Del.

The imaging medium 10 also comprises a diffusion-reducing subcoat 14 approximately 1 μm thick formed from a 10:1 w/w mixture of a water-dispersible styrene acrylic polymer (Joncryl 538 sold by S. C. Johnson & Son, Inc., Racine Wis. 53403) and a water-soluble acrylic polymer (Carboset 526 sold by The B. F. Goodrich Co., Akron Ohio 44313). The presence of the minor proportion of water-soluble acrylic polymer reduces the tendency for the layer 14 to crack during the coating process. The diffusion-reducing subcoat 14, which has a glass transition temperature of approximately 55° C., serves the function of a conventional subcoat, namely increasing the adhesion of the imaging layer 16 (described in detail below) to the support 12. The subcoat 14 also serves to reduce or eliminate migration of dye compound from the imaging layer 16 after imaging; if a conventional subcoat were employed in place of the diffusion-reducing subcoat 14, diffusion of the dye compound from the layer 16 into the subcoat after imaging might cause loss of sharpness of the image. The subcoat 14 is coated onto the support 12 from an aqueous medium containing the water-dispersible and water-soluble polymers.

A yellow imaging layer 16 is in contact with the diffusion-reducing subcoat 14. This imaging layer 16 is approximately 5 μm thick and comprises approximately 47.5 parts by weight of a leuco dye of the formula:

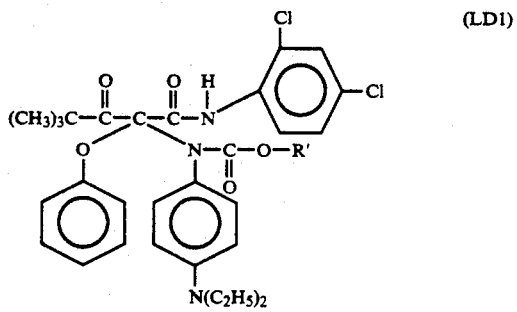
(LD1)

in which R' is a tertiary butyl group (the compounds in which R' is an isobutyl or benzyl group may alternatively be used), 1.6 parts by weight of an infra-red dye of the formula:

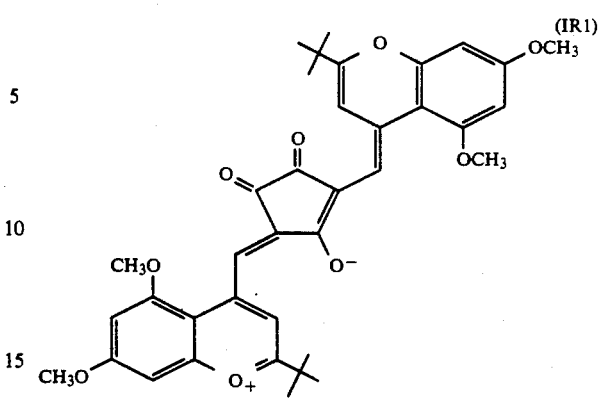
(IR1)

(prepared as described in the aforementioned copending application U.S. Ser. No. 07/795,038; essentially, this dye is produced by condensing two moles of a 2-(1,1-dimethylethyl)-5,7-dimethoxy-4-methylbenzpyrylium salt with a croconate salt), 3.3 parts by weight of a hindered amine stabilizer (HALS-63, sold by Fairmount Chemical Co.), and 47.5 parts by weight of a poly(methyl methacrylate) binder (Elvacite 2021, sold by DuPont de Nemours, Wilmington, Del.; this material is stated by the manufacturer to be a methyl methacrylate/ethyl acrylate copolymer, but its glass transition temperature approximates that of poly(methyl methacrylate)). This binder has a glass transition temperature of approximately 110° C. The imaging layer 16 is applied by coating from a mixture of heptanes and methyl ethyl ketone.

Superposed on the yellow imaging layer 16 is a diffusion-reducing layer 18, which, like the first diffusion-reducing layer 14, serves to prevent migration of dye compound from the yellow imaging layer 16 on storage after imaging. The diffusion-reducing layer 18, which is approximately 2 μm thick, is formed of a water-dispersible styrene acrylic polymer (Joncryl 138 sold by S. C. Johnson & Son, Inc., Racine Wis. 53403), and is coated from an aqueous dispersion. This layer has a glass transition temperature of approximately 60° C.

The next layer of the imaging medium 10 is a solvent-resistant interlayer 20 approximately 4.6 μm thick and composed of a major proportion of partially cross-linked polyurethane (NeoRez XR-9637 polyurethane sold by ICI Resins US, Wilmington, Mass.) and a minor proportion of poly(vinyl alcohol) (Airvol 540, sold by Air Products and Chemicals, Inc., Allentown Pa. 18195). This solvent-resistant interlayer 20 is coated from an aqueous dispersion. The interlayer 20 not only helps to thermally insulate the imaging layers 14 and 22 (described below) from one another during imaging, but also prevents disruption and/or damage to the yellow imaging layer 16 and the diffusion-reducing layer 18 during coating of the magenta imaging layer 22. Since the yellow imaging layer 16 and the magenta imaging layer 22 are both coated from organic solution, if a solvent-resistant interlayer were not provided on the layer 16 before the layer 22 was coated, the organic solvent used to coat the layer 22 might disrupt, damage or extract leuco dye or infra-red absorber from the layer 16. Provision of the solvent-resistant interlayer 20, which is not dissolved by and does not swell in the organic solvent used to coat the layer 22, serves to prevent disruption of or damage to the layer 16 as the layer 22 is coated. Furthermore, the solvent-resistant interlayer 20 serves to prevent the magenta leuco dye, infra-red dye and hindered amine light stabilizer from the layer 22 sinking into the diffusion-reducing layer 18 and the yellow imaging layer 16 as the layer 22 is being coated.

Superposed on the solvent-resistant interlayer 20 is the magenta imaging layer 22, which is approximately 3 μm thick and comprises approximately 47.25 parts by weight of a leuco dye of the formula:

coating from a cyclohexanone/methyl ethyl ketone mixture.

On the imaging layer 22 is coated a second solvent-resistant interlayer 24 which is formed from the same material, and coated in the same manner as, the solvent-resistant interlayer 20.

Superposed on the second solvent-resistant interlayer 24 is a cyan imaging layer 26, which is approximately 3 μm thick and comprises approximately 49.5 parts by weight of a leuco dye of the formula:

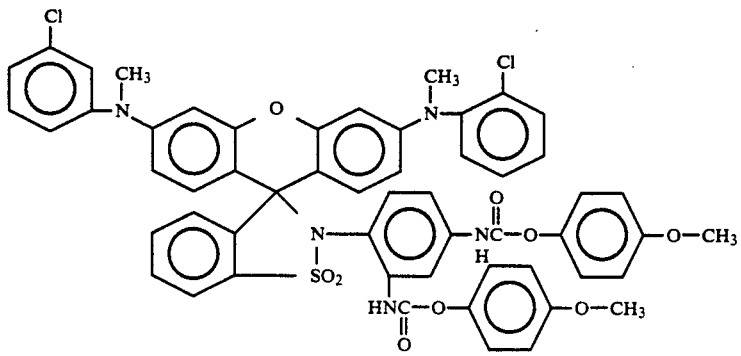

(LD2)

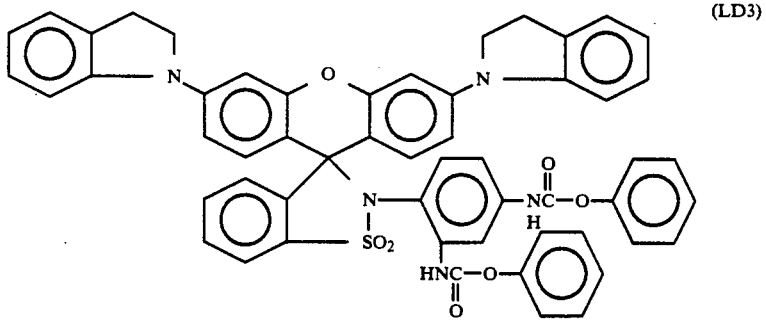

(LD3)

(this leuco dye may be prepared by the methods described in the aforementioned U.S. Pat. Nos. 4,720,449 and 4,960,901), approximately 3.4 parts by weight of zinc acetate (thus giving a leuco dye: zinc cation molar ratio of about 1:0.4), 1.62 parts by weight of an infra-red dye of the formula:

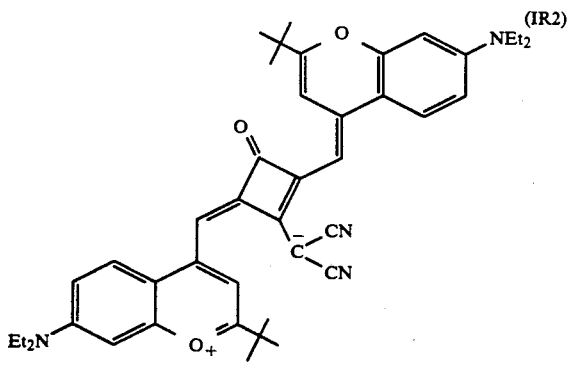

(IR2)

of the present invention (prepared in Example 5 below), 3.6 parts by weight of a hindered amine stabilizer (HALS-63), 0.27 parts by weight of a wetting agent, and 47.25 parts by weight of a polyurethane binder (Estane 5715, supplied by The B. F. Goodrich Co., Akron Ohio 44313). The imaging layer 22 is applied by (this leuco dye may be prepared by the methods described in the aforementioned U.S. Pat. Nos. 4,720,449 and 4,960,901), approximately 3.97 grams of zinc acetate (thus giving a leuco dye; zinc cation molar ratio of about 1:0.4), 1.62 parts by weight of an infra-red dye of the formula:

(IR3)

(which is preferably prepared by the process described in the aforementioned copending application U.S. Ser. No. 07/696,222; essentially this process comprises reacting a diester, diacid chloride or monoester monoacid chloride of squaric acid with a 2-(1,1-dimethylethyl)-7- diethylamino-4-methylbenzpyrylium salt and hydrolysing to produce a compound of the formula:

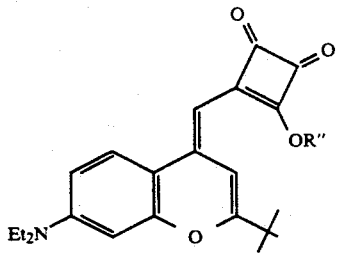

and then reacting this compound with a 7-alkoxy-2-(1,1-dimethylethyl)-4-methylbenzpyrylium salt to give the final infra-red dye of Formula IR3), 0.2 parts of a wetting agent, and 49.5 parts by weight of a polyurethane binder (Esane 5715). The imaging layer 26 is applied by coating from methyl ethyl ketone.

(Alternatively, the infra-red dye of Formula IR4 above may be replaced by the dye of formula:

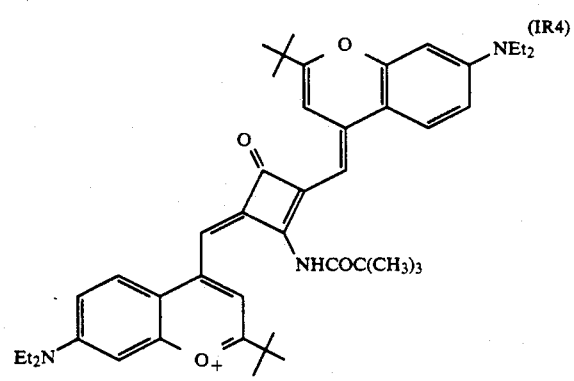

(used in the form of its tetrafluoroborate, which may be prepared by the process described in the aforementioned application U.S. Ser. No. 07/795,034; essentially, this infra-red dye is produced by reacting the compound of Formula V above with ammonia and then with pivaloyl chloride to introduce the —NHCO(CH$_3$)$_3$ group on the squarylium ring, and then reacting the product with a second mole of the 2-(1,1-dimethylethyl)-7-diethylamino-4-methylbenzpyrylium salt).

As already indicated, the layers 14–26 of the imaging medium 10 are produced by coating on to the transparent support 12. However, the remaining layers of the imaging medium 10, namely the transparent bubble-suppressant layer 32, the ultraviolet filter layer 30 and the adhesive layer 28 are not coated on to the layer 26 but rather are prepared as a separate unit and then laminated to the remaining layers of the medium.

The transparent bubble-suppressant layer 32 is a 1.75 mil (44 μm) PET film, a preferred film being that sold as ICI 505 film by ICI Americas, Inc., Wilmington, Del. The bubble-suppressant layer 32 prevents the formation of bubbles in the imaging layers 16, 22 and 26 of the imaging medium 10 during imaging.

The ultraviolet filter layer 30 serves to protect the imaging layers 16, 22 and 26 from the effects of ambient ultraviolet radiation. It has been found that the leuco dyes are susceptible to undergoing color changes when exposed to ultraviolet radiation during storage before or after imaging; such color changes are obviously undesirable since they increase the D$_{min}$ of the image and may distort the colors therein. The ultraviolet filter layer 30 is approximately 5 μm thick and comprises approximately 83 percent by weight of a poly(methyl methacrylate) (Elvacite 2043, sold by DuPont de Nemours, Wilmington, Mass.), 16.6 percent by weight of an ultraviolet filter (Tinuvin 328 sold by Ciba-Geigy, Ardsdale N.Y.) and 0.4 percent by weight of a wetting agent. The ultraviolet filter layer 30 is prepared by coating on to the bubble-suppressant layer 32 from a solution in methyl ethyl ketone.

The adhesive layer, which is approximately 2 μm thick, is formed of a water-dispersible styrene acrylic polymer (Joncryl 138 sold by S. C. Johnson & Son, Inc., Racine Wis. 53403) and is coated on to the ultraviolet filter layer 30 from an aqueous dispersion.

After the layers 30 and 28 have been coated on to the bubble-suppressant layer 32, the entire structure containing these three layers is laminated under heat (approximately 225° F., 107° C.) and pressure to the structure containing the layers 12–26 to form the complete imaging medium 10.

If desired, the bubble-suppressant layer 32 may be formed by coating, rather than by lamination of a preformed film on to the layers 12–26. If the bubble-suppressant layer 32 is to be formed by coating, it is convenient to incorporate an ultra-violet absorber into the bubble-suppressant layer, thereby avoiding the need for a separate ultra-violet absorber layer. Thus, in this case, the layer 28 is coated on to the layer 26 using the solvent already described, and then the bubble-suppressant layer 32 containing the ultra-violet absorber may be coated on to the layer 28 from an aqueous medium.

The medium 10 is imaged by exposing it simultaneously to the beams from three infra-red lasers having wavelengths of approximately 792, 860 and 926 nm. The 926 nm beam images the yellow imaging layer 16, the 860 nm beam images the magenta imaging layer 22 and the 792 nm beam images the cyan imaging layer 26. Thus, a multicolor image is formed in the imaging medium 10, and this multicolor image requires no further development steps. Furthermore, the medium 10 may be handled in normal room lighting prior to exposure, and the apparatus in which the imaging is performed need not be light-tight.

Alternatively, the present dyes may be used in a thermal imaging process in which the medium comprises one layer of a multi-layer structure, this structure further comprising a support layer disposed on one side of the medium and a colored layer adhering to the opposed side of the medium. In this type of thermal imaging process, the heat generated on exposure of the dye to actinic radiation causes increased adhesion of the colored layer to the support layer, such that upon application of a peeling force to the colored layer, the colored layer will peel from the support layer in areas which have not been exposed to the radiation, but in areas which have been exposed to radiation the colored layer will remain attached to the support layer. A preferred thermal imaging process of this type is described and claimed in International Patent Application No. PCT/US87/03249.

From the foregoing description, it will be seen that the present invention provides near infra-red dyes with enhanced compatibility with a variety of media and which can be arranged to have absorptions within narrow wavelength ranges. Furthermore, these dyes can contain a variety of functional groups. The processes of the present invention enable asymmetric infra-red dyes of the invention to be synthesized without the need to separate mixtures of asymmetric and symmetric dyes.

The following Examples are now given, though by way of illustration only, to show details of particularly preferred reagents, conditions and techniques used in the processes of the present invention.

EXAMPLE 1

Preparation of 4-[[7-diethylamino-2-(1,1-dimethylethyl)benz[b]-4H-pyran-4-ylidene1-methyl-3-butoxycyclobut-3-en-1,2-dione This Example illustrates the preparation, by a reaction analogous to B+H→K shown in FIG. 1, of the squaric acid derivative K in which $R^1$ is a hydrogen atom, this being the compound of Formula III in which $Q^1$ is a 7-diethylamino-2-[1,1-dimethylethyl]benz[b]-4H-pyran-4-ylidene grouping, $R^1$ is a hydrogen atom and A is a butoxy grouping.

A solution of 7-diethylamino-2-(1,1-dimethylethyl)-4-methylbenzpyrylium tetrafluoroborate (3.57 g, 10 mmol, prepared as described in the aforementioned copending application U.S. Ser. No. 07/616,639) in dichloromethane (20 mL) was added dropwise over two hours to a solution of di-n-butyl squarate (2.5 g, 11 mmol, available from Aldrich Chemical Company, Milwaukee, Wis.) and triethylamine (2.02 g, 20 mmol) in dichloromethane (30 mL) at room temperature. After the addition had been completed, the reaction mixture was heated under reflux for three hours. The solvent was then removed and diethyl ether (50 mL) was added. The ether solution was filtered and the solid residue was washed with more ether (50 mL). The combined ether extracts were concentrated, and the crude product thus obtained was purified by flash chromatography on silica gel with 30% ether/hexanes as eluent to give 4-[[7-diethylamino-2-(1,1-dimethylethyl)benz[b]-4H-pyran-4-ylidene]methyl]-3-butoxy-cyclobut-3-en-1,2-dione as a red solid (1.35 g, 29% yield) which melted at 145°–146° C. The structure of this compound was confirmed by mass spectroscopy and by $^1H$ and $^{13}C$ NMR spectroscopy.

(The filtrate from the ether extraction was collected, dissolved in dichloromethane, washed sequentially with 1M hydrochloric acid, a saturated solution of sodium hydrogen carbonate and brine, and dried over magnesium sulfate. Removal of solvent yielded 3,4-bis[[7-diethylamino-2-(1,1-dimethylethyl)benz[b]-4H-pyran-4-ylidene]methyl]cyclobut-3-en-1,2-dione as a green solid (1.14 g, 37% yield) which did not melt below 300° C. The structure of this compound was confirmed by mass spectroscopy and by $^1H$ and $^{13}C$ NMR spectroscopy.)

EXAMPLE 2

Preparation of 4-[[2,6-bis-[1,1-dimethylethyl]thiopyran-4-ylidene1-methyl-3-butoxycyclobut-3-en-1,2-dione This is the compound of Formula III in which $Q^1$ is a 2,6-bis(1,1-dimethylethyl)-4H-thiopyran-4-ylidene grouping, $R^1$ is a hydrogen atom, and A is a butoxy group. This compound was prepared in the same manner as in Example 1, except that the starting material used was 2,6-bis-[1,1-dimethylethyl]-4-methylthiopyrylium tetrafluoroborate, the preparation of which is described in U.S. Pat. No. 4,343,948 to Kawamura.

EXAMPLE 3

Preparation of 4-dicyanomethyl-3-[[7-diethylamino-2-[1,1-dimethylethyl]benz[b1-4H-pyran-4-ylidene]methyl]-cyclobut-3-en-1,2-dione, diazabicycloundecene salt This is the compound of Formula II in which $Q^1$ is a 7-diethylamino-2-[1,1-dimethylethyl]benz[b]-4H-pyran-4-ylidene grouping, $R^1$ is a hydrogen atom, $R^3$ and $R^4$ are cyano groups, and $R^5$ is a hydrogen atom. The compound was produced in the form of a salt, in which the hydrogen atom $R^5$ is removed, giving the squarylium moiety a net negative charge, the hydrogen atom being transferred to a diazabicycloundecene base.

A solution of 1,8-diazabicyclo[5.4.0]-undec-7-ene (DBU, 36 mg, 0.24 mmol) in tetrahydrofuran (THF, 0.5 mL) was added to a solution of 3-butoxy-4-[[7-diethylamino-2-[1,1-dimethylethyl]benz[b]-4H-pyran-4-ylidene]methyl]-cyclobut-3-en-1,2-dione (100 mg, 0.24 mmol, prepared in Example 1 above) and malononitrile (16 mg, 0.24 mmol) in THF (2 mL). After one hour, further quantities of DBU (36 mg, 0.24 mmol) and malononitrile (16 mg, 0.24 mmol) were added, and the reaction mixture was stirred for a further 2 hours. The solvent was then removed under reduced pressure and the residue was washed with ether, causing it to crystallize. The crystals were collected and washed with ether to give the desired salt (62 mg, 46% yield) as a red solid. The structure of this compound was confirmed by mass spectroscopy and by $^1H$ and $^{13}C$ NMR spectroscopy.

EXAMPLE 4

Preparation of 4-dicyanomethyl-3-[2,6-bis-[1,1-dimethylethyl]thio-4H-pyran-4-ylidene]methyl]-cyclobut-3-en-1,2-dione, diazabicycloundecene salt This is the compound of Formula II in which $Q^1$ is a 2,6-bis-[1,1-dimethylethyl]-4H-thiopyran-4-ylidene grouping, $R^1$ is a hydrogen atom, $R^3$ and $R^4$ are cyano groups, and $R^5$ is a hydrogen atom. As in Example 3, the compound was prepared in the form of a diazabicycloundecene salt.

This compound was prepared in the same manner as in Example 3 above, using as starting material the compound of Formula III prepared in Example 2 above. The structure of this compound was confirmed by mass spectroscopy and by $^1H$ and $^{13}C$ NMR spectroscopy.

EXAMPLE 5

4-[[4-dicyanomethyl-3-[[7-diethylamino-2-1,1-dimethylethyl]benz[b]-4H-pyran-4-ylidene]methyl]-cyclobut-3-en-2-one-1-ylidene methyl]-7-diethylamino-2-1,1-dimethylethyl]benz[b]pyrylium hydroxide inner salt dye This is the dye of Formula A shown in FIG. 2 in which $R^1$ and $R^2$ are each a hydrogen atom, $R^3$ and $R^4$ are each a cyano group and $R^5$ is a hydrogen atom, this being the compound of Formula I in which $Q^1$ is a 7-diethylamino-2-[1,1-dimethylethyl]benz[b]-4H-pyran-4-ylidene grouping, $Q^2$ is a 7-diethylamino-2-[1,1-dimethylethyl]benz[b]-4H-pyrylium grouping, $R^1$ and $R^2$ are each a hydrogen atom, $R^3$ and $R^4$ are each a cyano group, and $R^5$ is a hydrogen atom in the protonated form of the dye. Under neutral conditions, the $R^5$ proton is removed, yielding an uncharged dye.

A solution of 4-dicyanomethyl-3-[[7-diethylamino-2-[1,1-dimethylethyl]benz[b]-4H-pyran-4-ylidene]methyl]-cyclobut-3-en-1,2-dione hydroxide, diazabicycloundecene salt (50 mg, 0.09 mmol, prepared in Example 3 above), 7-diethylamino-2-[1,1-dimethylethyl]-4-methylbenzpyrylium tetrafluoroborate (prepared as described in the aforementioned copending U.S. application U.S. Ser. No. 07/795,038, 50 mg, 0.14 mmol) and quinoline (5 drops) was heated at reflux in n-butanol (5 mL) for 5 hours, then cooled and allowed to stand overnight. The crude product was separated by filtration and washed with ether to afford brown crystals of the desired dye (30 mg, 50% yield) which had a principal infra-red absorption at 851 nm in dichloromethane solution, $\epsilon = 312,000$. The structure of this compound was confirmed by mass spectroscopy and by $^1H$ and $^{13}C$ NMR spectroscopy.

EXAMPLE 6

Preparation of
4-[[4-dicyanomethyl-3-[2,6-bis-[1,1-dimethylethyl]thio-4H-pyran-4-ylidene]methyl]-cyclobut-3-en-2-one-1-ylidene]methyl]-2,6-bis-1,1-dimethylethyl]thiopyrylium hydroxide inner salt dye This is the compound of Formula I in which $Q^1$ is a 2,6-bis-[1,1-dimethylethyl]-4H-thiopyran-4-ylidene grouping, $Q^2$ is a 4-[2,6-bis-[1,1-dimethylethyl]]-4H-thiopyrylium grouping, $R^1$ and $R^2$ are each a hydrogen atom, $R^3$ and $R^4$ are each a cyano group, and $R^5$ is a hydrogen atom in the protonated form of the dye. Under neutral conditions, the $R^5$ proton is removed, yielding an uncharged dye.

The dye was prepared in the same manner as in Example 5 above using as starting material the compound of Formula II prepared in Example 4 above. The dye had a principal infra-red absorption at 869 nm in dichloromethane solution, $\epsilon = 147,000$. The structure of this compound was confirmed by mass spectroscopy and by $^1H$ NMR spectroscopy.

EXAMPLE 7

Preparation of
2,3-dibutoxy-4-hydroxy-4-phenylcyclobut-2-en-1-one

This is the intermediate of Formula Q shown in FIG. 3 in which the $CR^3R^4R^5$ grouping is a phenyl group.

Phenyl lithium (6.64 mL of a 2.2M solution in cyclohexane/diethyl ether, 14.6 mmol) was added dropwise over a period of 25 minutes to a solution of 3,4-dibutoxycyclobut-3-en-1,2-dione (i.e., dibutyl squarate, 3.0 g, 13.3 mmol) in tetrahydrofuran (THF, 30 mL) at −78° C. under nitrogen. The resultant solution was maintained at −78° C. for 30 minutes, then allowed to warm to room temperature and stirred for 2 hours. The mixture was then poured into cold water (10 mL), and THF (20 mL) and saturated sodium chloride solution (40 mL) were added to the resultant mixture. The organic layer was dried over magnesium sulfate and concentrated under reduced pressure to give a brown oil which was purified by flash chromatography on silica gel with 35% ether/hexanes as eluent (2 separations were required) to give the desired intermediate as a pale yellow oil (1.32 g, 33% yield) which was used as is in Example 8 below.

EXAMPLE 8

Preparation of
3-butoxy-4-phenylcyclobut-3-en-1,2-dione

This is the compound of Formula R shown in FIG. 3 in which the $CR^3R^4R^5$ grouping is a phenyl group, this being the compound of Formula IV in which E is a butoxy group, and the $CR^3R^4R^5$ grouping is a phenyl group.

Concentrated hydrochloric acid (0.1 mL) was added to a stirred solution of 2,3-dibutoxy-4-hydroxy-4-phenylcyclobut-2-en-1-one (1.24 g, 4.07 mmol, prepared in Example 7 above) in dichloromethane (25 mL) at 0° C., and the mixture was stirred at that temperature for 1 hour. The mixture was then warmed to room temperature, washed sequentially with saturated sodium bicarbonate solution (15 mL) and saturated sodium chloride solution (15 mL), dried over magnesium sulfate and concentrated under reduced pressure to yield a yellow solid, which was recrystallized from hexanes to give the desired squaric acid derivative (477 mg, 51% yield). The structure of this compound was confirmed by mass spectroscopy and by $^1H$ NMR spectroscopy.

EXAMPLE 9

Preparation of
3-[[7-diethylamino-2-[1,1-dimethylethyl]benz[b]-4H-pyran-4-ylidene1-methyl]-4-phenylcyclobut-3-en-1,2-dione This is the compound of Formula L shown in FIG. 2 in which $R^1$ is a hydrogen atom and the $CR^3R^4R^5$ grouping is a phenyl group, this being the compound of Formula II in which $Q^1$ is a 7-diethylamino-2-[1,1-dimethylethyl]benz[b]4H-pyran-4-ylidene grouping, $R^1$ is a hydrogen atom and the $CR^3R^4R^5$ grouping is a phenyl group.

A solution of 3-butoxy-4-ethylcyclobut-3-en-1,2-dione (325 mg, 1.41 mmol, prepared in Example 8 above), 7-diethylamino-2-[1,1-dimethylethyl]-4-methylbenzpyrylium tetrafluoroborate (507 mg, 1.41 mmol, prepared as described in the aforementioned copending U.S. application U.S. Ser. No. 07/795,038) and triethylamine (285 mg, 2.82 mmol) in dichloromethane was held at room temperature overnight (about 17 hours) and then concentrated under reduced pressure. The residue was purified by flash chromatography on silica gel with 20%–50% ethyl acetate/hexanes as eluent to give the desired squaric acid derivative as a red solid (411 mg, 65% yield). The structure of this compound was confirmed by mass spectroscopy and by $^1H$ and $^{13}C$ NMR spectroscopy.

EXAMPLE 10

Preparation of
4-[[3-[[7-diethylamino-2-[1,1-dimethylethyl]benz[b]-4H-pyran-4-ylidene]methyl]-2-phenyl-2-cyclobuten-1-ylidene]methyl]-7-diethylamino-2-1,1-dimethylethyl]-benz[b]pyrylium tetrafluoroborate This is the dye of Formula A shown in FIG. 2 in which $R^1$ and $R^2$ are each a hydrogen atom and the $CR^3R^4R^5$ grouping is a phenyl group, this being the compound of Formula I in which $Q^1$ is a 7-diethylamino-2-[1,1-dimethylethyl]benz[b]-4H-pyran-4-ylidene grouping, $Q^2$ is a 7-diethylamino-2-[1,1-dimethylethyl]-benz[b]-4H-pyrylium grouping, $R^1$ and $R^2$ are each a hydrogen atom and the $CR^3R^4R^5$ grouping is a phenyl group.

A solution of 3-[[7-diethylamino-2-[1,1-dimethylethyl]benz[b]-4H-pyran-4-ylidene]-methyl]-4-phenylcyclobut-3-en-1,2-dione (200 mg, 0.47 mmol, prepared in Example 9 above), 7-diethylamino-2-[1,1-dimethylethyl]-4-methylbenzpyrylium tetrafluoroborate (169 mg, 0.47 mmol, prepared as described in the aforementioned copending U.S. application U.S. Ser. No. 07/795,038) and quinoline (181 mg, 1.4 mmol) in n-butanol (5 mL) was heated at reflux for 2 hours, then cooled to room temperature and allowed to stand for 3 days. Heating to reflux was then resumed and continued for a further 8 hours, after which the reaction mixture was allowed to stand overnight, then concentrated under reduced pressure. The n-butanol was removed by azeotropic distillation with toluene and the residue was purified by flash chromatography on silica gel with 5% methanol/dichloromethane as eluent, followed by preparative thin-layer chromatography (two purifications) with the same eluent. The desired dye, which was obtained as a dark green solid (34 mg, 9.4% yield), had a principal infra-red absorption at 758 nm in dichloromethane solution, $\epsilon = 336,000$. The structure of this compound was confirmed by mass spectroscopy and by $^1H$ and $^{13}C$ NM spectroscopy.

EXAMPLE 11

Preparation of 2,3-dibutoxy-4-ethyl-4-hydroxycyclobut-2-en-1-one

This is the compound of Formula Q shown in FIG. 3 in which the $CR^3R^4R^5$ grouping is an ethyl group.

Ethyl magnesium bromide (23.2 mL of a 1M solution in THF, 23.2 mmol) was added dropwise over a period of 15 minutes to a solution of 3,4-dibutoxycyclobut-3-en-1,2-dione (5.0 g, 22.1 mmol) in tetrahydrofuran (THF, 50 mL) at $-78°$ C. under nitrogen. The solution was maintained at $-78°$ C. for 30 minutes, then allowed to warm to room temperature and stirred for 2 hours. The mixture was then poured into cold water (10 mL) and the resultant mixture was poured into water (200 mL). Ether (200 mL) and saturated sodium chloride solution (50 mL) were added to the resultant emulsion and the organic layer was separated, washed with saturated sodium chloride solution, dried over magnesium sulfate and concentrated under reduced pressure to give a yellow oil, which was purified by flash chromatography on silica gel with 50% ether/hexanes as eluent to give the desired intermediate as a pale yellow oil (955 mg, 17% yield). The structure of this compound was confirmed by $^1H$ and $^{13}C$ NMR spectroscopy.

EXAMPLE 12

Preparation of 3-butoxy-4-ethylcyclobut-3-en-1,2-dione

This is the compound of Formula R shown in FIG. 3 in which the $CR^3R^4R^5$ grouping is an ethyl group, this being the compound of Formula IV in which E is a butoxy group and the $CR^3R^4R^5$ grouping is an ethyl group.

Concentrated hydrochloric acid (0.1 mL) was added to a stirred solution of 2,3-dibutoxy-4-ethyl-4-hydroxycyclobut-2-en-1-one (0.887 g, 3.46 mmol, prepared in Example 11 above) in dichloromethane (20 mL) at 0° C., and the mixture was stirred at that temperature for 1 hour. The mixture was then warmed to room temperature and washed sequentially with saturated sodium bicarbonate solution (15 mL) and saturated sodium chloride solution (10 mL), dried over magnesium sulfate and concentrated under reduced pressure to yield a yellow oil, which was partially purified by flash chromatography on silica gel with dichloromethane as eluent to give the desired squaric acid derivative (669 mg, slightly impure). This material was used as is in Example 13 below.

EXAMPLE 13

Preparation of 3-[7-diethylamino-2-[1,1-dimethylethyl]benz[b]-4H-pyran-4-ylidene]-methyl]-4-ethylcyclobut-3-en-1,2-dione This is the compound of Formula L shown in FIG. 2 in which in which the $CR^3R^4R^5$ grouping is an ethyl group, this being the compound of Formula II in which $Q^1$ is a 7-diethylamino-2-[1,1-dimethylethyl]benz[b]-4H-pyran-4-ylidene grouping, $R^1$ is a hydrogen atom and the $CR^3R^4R^5$ grouping is an ethyl group.

Triethylamine (706 mg, 7.0 mmol) was added to a solution of impure 3-butoxy-4-ethylcyclobut-3-en-1,2-dione (636 mg, prepared in Example 12 above) and 7-diethylamino-2-[1,1-dimethylethyl]-4-methylbenzpyrylium tetrafluoroborate (1.25 g, 3.49 mmol, prepared as described in the aforementioned copending U.S. application U.S. Ser. No. 07/795,038) in dichloromethane (35 mL) and the resultant solution was held at room temperature overnight (about 17 hours) and then heated at reflux for 4 hours, cooled, and concentrated under reduced pressure. The residue was purified by flash chromatography on silica gel with 0–5 % methanol/dichloromethane as eluent, followed by a second chromatographic purification on silica gel with 0–10% acetonitrile/dichloromethane as eluent to give the desired squaric acid derivative as a red solid (360 mg, 25% yield over the two steps of Examples 12 and 13). The structure of this compound was confirmed by mass spectroscopy and by $^1H$ and $^{13}C$ NMR spectroscopy.

EXAMPLE 14

Preparation of 4-[[3-[[7-diethylamino2-[1,1-dimethylethyl]benz[b]-4H-pyran-4-ylidene]methyl]-2-ethyl-2-cyclobuten-1-ylidene]methyl]-7-diethylamino-2-[1,1-dimethylethyl]-benz[b]pyrylium tetrafluoroborate This is the dye of Formula A shown in FIG. 2 in which $R^1$ and $R^2$ are each a hydrogen atom, and the $CR^3R^4R^5$ grouping is an ethyl group, this being the compound of Formula I in which $Q^1$ is a 7-diethylamino-2-[1,1-dimethylethyl]benz[b]-4H-pyran-4-ylidene grouping, $Q^2$ is a 7-diethylamino-2-[1,1-dimethylethyl]benz[b]-4H-pyrylium grouping, $R^1$ and $R^2$ are each a hydrogen atom, and the $CR^3R^4R^5$ grouping is an ethyl group.

A solution of 3-[[7-diethylamino-2-[1,1-dimethylethyl]benz[b]-4H-pyran-4-ylidene]methyl]-4-ethylcyclobut-3-en-1,2-dione (200 mg, 0.53 mmol, prepared in Example 13 above), 7-diethylamino-2-[1,1-dimethylethyl]-4-methylbenzpyrylium tetrafluoroborate (190 mg, 0.53 mmol, prepared as described in the aforementioned copending U.S. application U.S. Ser. No. 07/795,038) and quinoline (204 mg, 1.58 mmol) in n-butanol (6 mL) was heated at reflux for 8 hours, then cooled to room temperature and allowed to stand overnight. Heating to reflux was then resumed and continued for a further 8 hours, after which the reaction mixture was allowed to stand overnight, then concentrated under reduced pressure. The residue was partially purified by flash chromatography on silica gel with 5% methanol/ dichloromethane as eluent, followed by preparative thin-layer chromatography (two purifications) with the same eluent. The desired dye, which was obtained as a dark green solid (49 mg, 13% yield), had a principal infra-red absorption at 752 nm in dichloromethane solution, $\epsilon=325,000$. The structure of this compound dye was confirmed by $^1$H and $^{13}$C NMR spectroscopy.

EXAMPLE 15

Imaging

This Example illustrates the use of a dye of the present invention in a thermal imaging medium and process.

The thermal imaging medium used was a simplified model of that described above with reference to FIG. 4. A coating fluid was prepared by combining the infra-red dye prepared in Example 5 above (0.18 mL of a 1% solution in dichloromethane) with a leuco dye of formula LD3 above (110 mg) and a polymeric binder (polyurethane Estane 5715, supplied by B. F. Goodrich, 0.73 mL of a 15% solution in acetone). The fluid was coated onto a 4 mil (101 μm) transparent poly(ethylene terephthalate) base using a #12 coating rod. The film so formed was laminated at 180° F. (88° C.) and 60 psi (0.4 MPa) to a second sheet of 4 mil (101 μm) poly(ethylene terephthalate) which had been coated with Joncryl 138 (supplied by S. C. Johnson & Son, Inc., Racine Wis. 53403) to a thickness of approximately 2 μm. The resultant imaging medium exhibited a peak absorption in the near infra-red at 863.5 nm, absorbance 0.62. Storage of a sample of the medium at 60° C. for 4 days resulted in a loss of only 1.6% of near infra-red absorption.

A portion of the medium which had not been heated was exposed to infra-red radiation from a GaAlAs semiconductor diode laser emitting at 867 nm, which delivered 62 mW to the medium. The laser output was focussed to a spot approximately 33×3 microns in size. The medium was wrapped around a drum whose axis was perpendicular to the incident laser beam. Rotation of the drum about its axis and simultaneous translation of the drum in the direction of the axis caused the laser spot to write a helical pattern on the medium. The pitch of the helix was 33 microns, chosen so that none of the medium was left unexposed between adjacent turns of the helix. In this arrangement, the exposure received by the medium was inversely proportional to the speed of rotation of the drum (here measured as a linear writing speed at the medium surface). The Table below shows the relationship between writing speed and red optical density (measured using an X-Rite 310 photographic densitometer, supplied by X-Rite, Inc., Grandville, Mich., with the appropriate filter) achieved. The unexposed medium had a red density of 0.08.

TABLE

| Writing speed, m/s | Red optical density |
| --- | --- |
| 0.14 | 0.51 |
| 0.125 | 0.75 |

From these results, it will be seen that this thermal imaging medium was capable of producing images when exposed to near infra-red radiation.

We claim:

1. A squarylium compound of the formula:

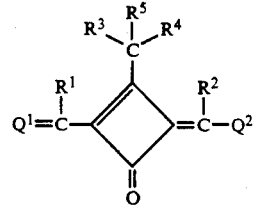

in which $Q^1$ and $Q^2$ are each a pyrylium, thiopyrylium, selenopyrylium, benzpyrylium, benzthiopyrylium or benzeleneopyrylium nucleus, $R^1$ and $R^2$ are each independently a hydrogen atom or an alkyl group containing not more than about 6 carbon atoms, and:

(a) $R^3$, $R^4$ and $R^5$ are each independently a hydrogen atom, an alkyl, cycloalkyl or acyl group, or a cyano group, (b) one of $R^3$, $R^4$ and $R^5$ is a hydrogen atom or an alkyl group, and the other two of $R^3$, $R^4$ and $R^5$ form, together with the intervening carbon atom, a cycloalkyl group;

(c) one of $R^3$, $R^4$ and $R^5$ is a hydrogen atom or an alkyl group, and the other two of $R^3$, $R^4$ and $R^5$ together form an alkylidene group, so that the $CR^3R^4R^5$ grouping is an alkene group;

(d) $R^3$, $R^4$ and $R^5$, together with the intervening carbon atom, form a phenyl ring; or (e) $R^3$, $R^4$ and $R^5$ together from an alkylene group, so that the $CR^3R^4R^5$ grouping is an alkylene group.

2. A squarylium compound of the formula:

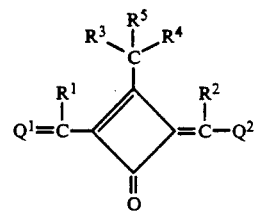

in which $Q^1$ and $Q^2$ are each a pyrylium, thiopyrylium, selenopyrylium, benzpyrylium, benzthiopyrylium or benzeleneopyrylium nucleus, $R^1$ and $R^2$ are each independently a hydrogen atom or an alkyl group containing not more than about 6 carbon atoms, and $R^3$, $R^4$ and $R^5$ are each independently a hydrogen atom, an alkyl group, or a cyano group, or $R^3$, $R^4$ and $R^5$, together with the intervening carbon atom, form a phenyl group.

3. A squarylium compound of the formula:

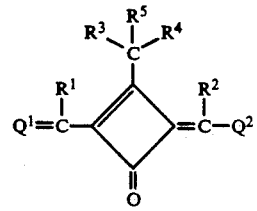

in which $Q^1$ and $Q^2$ are each a 7-dialkylaminobenzpyranyl grouping, $R^1$ and $R^2$ are each independently a hydrogen atom or an alkyl group containing not more than about 6 carbon atoms, and $R^3$, $R^4$ and $R^5$ are each independently a hydrogen atom, an alkyl group, or a cyano group, or $R^3$, $R^4$ and $R^5$, together with the intervening carbon atom, form a phenyl group.

4. A squarylium compound according to claim 1 wherein each of $R^4$ and $R^5$ is a cyano group.

5. A squarylium compound according to claim 1 wherein each of $R^3$, $R^4$ and $R^5$ is a hydrogen atom or an alkyl group.

6. A squarylium compound according to claim 1 wherein all three of $R^3$, $R^4$ and $R^5$, together with the carbon atom to which they are attached, form a phenyl nucleus.

7. A squarylium compound according to claim 1 wherein each of $Q^1$ and $Q^2$ is a 4-pyrylium, 4-thiopyrylium, 4-selenopyrylium, 4-benzpyrylium, 4-benzthiopyrylium or 4-benzeleneopyrylium nucleus.

8. A squarylium compound according to claim 7 wherein at least one of $Q^1$ and $Q^2$ is a 2,6-dialkylpyrylium, -thiopyrylium or -selenopyrylium nucleus, in which each of the alkyl groups contains not more than about 8 carbon atoms.

9. A squarylium compound according to claim 8 wherein at least one of $Q^1$ and $Q^2$ is a 2,6-di-tertiary butylpyrylium, -thiopyrylium, or -selenopyrylium nucleus.

10. A squarylium compound according to claim 7 wherein at least one of $Q^1$ and $Q^2$ is a benzpyrylium nucleus carrying at its 2-position a substituent in which a non-aromatic carbon atom is bonded directly to the benzpyrylium nucleus, subject to the proviso that if said 2-substituent contains an aromatic nucleus, this aromatic nucleus is not conjugated with the benzpyrylium nucleus.

11. A squarylium compound according to claim 10 wherein the 2-substituent is a substituted or unsubstituted alkyl or cycloalkyl group.

12. A squarylium compound according to claim 10 wherein the benzpyrylium nucleus carries at the 7-position a substituent in which an element of Group 5A, 6A or 7A of the Periodic Table is directly connected to the benzpyrylium nucleus, subject to the proviso that when said element is of Group 5A, or 6A, the 7-substituent may be at least one saturated ring containing said element of Group 5A or 6A, this saturated ring optionally being fused to the benzene ring of the associated benzpyrylium nucleus.

13. A squarylium compound according to claim 12 wherein the 7-substituent is an alkoxy group containing not more than about 12 carbon atoms, or a disubstituted amino or disubstituted phosphino groups, wherein each of the substituents on the distributed group is an alkyl group containing not more than about 6 carbon atoms, or the two substituents on any one distributed group together form, with the nitrogen or phosphorus atom thereof, a heterocyclic ring system, this ring system optionally being fused to the benzpyrylium nucleus which carries the disubstituted amino or phosphino substituent.

14. A squarylium compound according to claim 13 wherein each of the 7-disubstituted amino groups is independently selected from the group consisting of dialkylamino wherein each of the alkyl groups contains not more than about 4 carbon atoms, piperidino, indolinyl, morpholino and $-N[-(CH_2)_3-]_2$ groups, subject to the proviso that when one or both of the amino groups is a $-N[-(CH_2)_3-]_2$ group, the ends of the trimethylene groups remote from the nitrogen atom are joined to the 6- and 8-positions of the benzpyrylium nucleus carrying the nitrogen atom, so that the $-N[-(CH_2)_3-]_2$ group and the benzene ring of the benzpyrylium nucleus together form a julolidine ring system.

15. A squarylium compound according to claim 1 wherein:

a. $Q^1$ is a 7-diethylamino-2-[1,1-dimethylethyl]-benz[b]-4H-pyran-4-ylidene grouping, $Q^2$ is a 7-diethylamino-2-[1,1-dimethylethyl]benz[b]-4H-pyrylium grouping, $R^1$ and $R^2$ are each a hydrogen atom, $R^3$ and $R^4$ are each a cyano group, and $R^5$ is a hydrogen atom, namely 4-[[4-dicyanomethyl-3-[[-7-diethylamino-2-[1,1-dimethylethyl]benz[b]-4H-pyran-4-ylidene]methyl]-cyclobut-3-en-2-one-1-ylidene]methyl]7-diethylamino-2-[1,1-dimethylethyl]benz[b]-pyrylium hydroxide inner salt;

b. $Q^1$ is a 2,6-bis-dimethylethyl]-4H-thiopyran-4-ylidene grouping, $Q^2$ is a 4-[2,6-bis-[1,1-dimethylethyl]-4H-thiopyrylium grouping, $R^1$ and $R^2$ are each a hydrogen atom, $R^3$ and $R^4$ are each a cyano group, and $R^5$ is a hydrogen atom, namely 4-[[4-dicyanomethyl-3-[[2,6-bis-[1,1-dimethylethyl]thio-4H-pyran-4-ylidene]methyl]-cyclobut-3-en-2-one-1-ylidene]methyl]2,6-bis-[1,1-dimethylethyl]thiopyrylium hydroxide inner salt;

c. $Q^1$ is a 7-diethylamino-2-[1,1-dimethylethyl]-benz[b]-4H-pyran-4-ylidene grouping, $Q^2$ is a 7-diethylamino-2-[1,1-dimethylethyl]benz[b]-4H-pyrylium grouping, $R^1$ and $R^2$ are each a hydrogen atom, and the $CR^3R^4R^5$ grouping is a phenyl group, namely a 4-[[3-[[7-diethylamino-2-[1,1-dimethylethyl]benz[b]-4H-pyran-4-ylidene]methyl]-2-phenyl-2-cyclobuten-1-ylidene]methyl]7-diethylamino-2-[1,1-dimethylethyl]benz[b]-pyrylium salt; and d. $Q^1$ is a 7-diethylamino-2-[1,1-dimethylethyl]-benz[b]-4H-pyran-4-ylidene grouping, $Q^2$ is a 7-diethylamino-2-[1,1-dimethylethyl]benz[b]-4H-pyrylium grouping, $R^1$ and $R^2$ are each a hydrogen atom, and the $CR^3R^4R^5$ grouping is an ethyl group, namely a 4-[[3-[[7-diethylamino-2-[1,1-dimethylethyl]benz[b]-4H-pyran-4-ylidene]methyl]-2-ethyl-2-cyclobuten-1-ylidene]methyl]7-diethylamino-2-[1,1-dimethylethyl]benz[b]-pyrylium salt.

* * * * *